United States Patent [19]
Farr et al.

[11] Patent Number: 5,969,132
[45] Date of Patent: *Oct. 19, 1999

[54] MACROCYCLIC DIFLUOROSTATONE DERIVATIVES USEFUL AS ANTIVIRAL AGENTS

[75] Inventors: Robert A. Farr, Loveland, Ohio; Brent L. Podlogar, Bridgewater, N.J.

[73] Assignee: Merrell Pharmaceuticals Inc., Bridgewater, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/676,208

[22] PCT Filed: Nov. 28, 1994

[86] PCT No.: PCT/US94/13711

§ 371 Date: Sep. 9, 1996

§ 102(e) Date: Sep. 9, 1996

[87] PCT Pub. No.: WO95/21186

PCT Pub. Date: Aug. 10, 1995

Related U.S. Application Data

[63] Continuation of application No. 08/192,080, Feb. 4, 1994, abandoned.

[51] Int. Cl.⁶ ................................................ C07D 273/00
[52] U.S. Cl. ............................................. 540/456; 530/321
[58] Field of Search ................................... 540/455, 456; 514/183; 530/321

[56] References Cited

FOREIGN PATENT DOCUMENTS

| | | |
|---|---|---|
| 2171103 | 8/1986 | United Kingdom . |
| 8606379 | 11/1986 | WIPO . |
| 9000399 | 1/1990 | WIPO . |
| 9209624 | 6/1992 | WIPO . |

OTHER PUBLICATIONS

Doherty et al., J. Med. Chem. 35, pp. 2–14 (1992).
Thaisrivongs, et al., J. Med. Chem. 29, p. 2080 (1986).
Szewczuk et al., Int. J. Peptide Protein Res. 40, pp. 233–242 (1992).
Podlogar et al., J. Med. Chem. 37, pp. 3684–3692 (1994).
H. Kessler, Angew. Chem. Int. Ed. Engl. 21, pp. 512–523 (1982).
Schirlin, et al., Bioorganic & Med. Chem. Letters, vol. 4, No. 2, pp. 241–246 (1994).

*Primary Examiner*—John M. Ford
*Attorney, Agent, or Firm*—Mark C. Nelligan

[57] ABSTRACT

The present invention provides novel macrocyclic difluorostatone derivatives which are useful as antiviral agents. More specifically, these novel compounds are useful as inhibitors of retroviral proteases required for replication, particularly the HIV-1 and HIV-2 viral proteases, in the prevention or treatment of infection by the human immunodeficiency virus (HIV), and in the treatment of consequent pathological conditions such as the acquired immunodeficiency syndrome (AIDS) in mammals capable of being infected with HIV virus.

16 Claims, No Drawings

MACROCYCLIC DIFLUOROSTATONE DERIVATIVES USEFUL AS ANTIVIRAL AGENTS

This application is a continuation of application Ser. No. 08/192,080, filed Feb. 4, 1994, now abandoned, and had an effective international filing date of Nov. 28, 1994, as application PCT/US94/13711, which designated the U.S. and entered the U.S. national phase on Sep. 9, 1996 under 35 USC 371.

BACKGROUND OF THE INVENTION

A great deal of research is currently underway to develop treatments and cures for viral infections in humans and in animals. Notably the incidence of AIDS and ARC in humans is increasing at an alarming rate. The five year survival rate for those with AIDS is dispiriting and AIDS patients, whose immune systems have been seriously impaired by the infection, suffer from numerous opportunistic infections including Kaposi's sarcoma and Pneumocystis carninii pneumonia. No cure for AIDS is known and current treatments are largely without adequate proof of efficacy and have numerous untoward side effects. Fear of the disease has resulted in social ostracism of and discrimination against those having or suspected of having the disease.

The present invention relates to compounds that are useful as antiviral agents. More specifically this invention relates to macrocyclic difluorostatone derivatives that are useful as inhibitors of retroviral proteases required for replication, such as the HIV-1 and HIV-2 viral proteases, the prevention or treatment of infection by the human immunodeficiency virus (HIV), and the treatment of consequent pathological conditions such as the acquired immunodeficiency syndrome (AIDS) in mammals capable of being infected with HIV virus.

SUMMARY OF THE INVENTION

The present invention relates to compounds having the following general formula I:

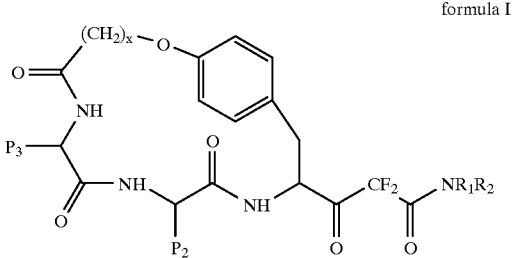

formula I and the stereoisomers, hydrates, and pharmaceutically acceptable salts thereof wherein $P_2$ is $C_{1-6}$ alkyl, cyclopentyl, hydroxy $C_{1-6}$ alkyl, phenyl, benzyl or 3-tetrahydrofuryl;

$P_3$ is selected from the group consisting of hydrogen, —$CH_3$, —$CH(CH_3)_2$, —$CH_2CH(CH_3)_2$, —$CH(CH_3)(CH_2CH_3)$, —$CH_2SH$, —$CH_2CH_2SCH_3$, —$CH_2OH$, —$CH(CH_3)OH$, —$CH_2(CH_2)_3NH_2$, —$CH_2(CH_2)_2NHC(=NH)NH_2$, —$CH_2CO_2H$, —$CH_2CH_2CO_2H$, —$CH_2CONH_2$, —$CH_2CH_2CONH_2$, benzyl,

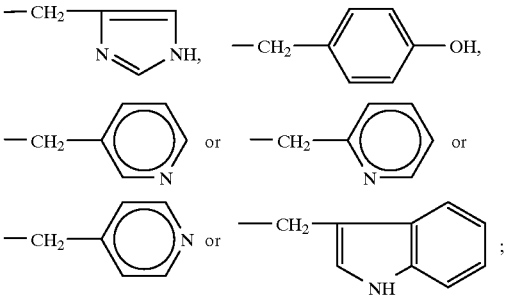

$R_1$ is hydrogen, $C_{1-15}$ alkyl, hydroxy $C_{1-15}$ alkyl, $CH([(CH_2)_d-O-CH_2]_f-R_7)_2$, $CH_2Si(CH_3)_2(R_8)$, PDL, —($C_{1-6}$ alkylene)—$OR_4$, $CH(Y)(Z)$,

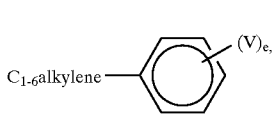
(a)

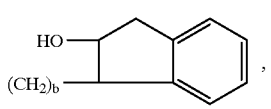
(b)

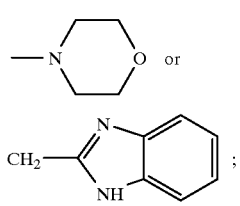
(c)

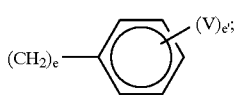
(d)

wherein PDL is —$(CH_2)_a$-2-, 3- or 4-pyridyl, Y is hydroxy $C_{1-15}$ alkyl, $C_{1-6}$ alkyl or $(CH_2)_e$-$C_6H_4$-$(V)_{e'}$; Z is $(CH_2)_d$-O—CHO, $C_{1-6}$ alkylene-O-$(CH_2)_d$-(O—$CH_2$—$CH_2)_e$-O—$C_{1-6}$ alkyl, CHO, $CO_2R_4$, $CONHR_4$, $(CH_2)_d$-O—$(CH_2)_d$-$R_5$, $(CH_2)_e$-$OR_4$ or (e)

(CH₂)ₑ—⟨ring⟩—(V)ₑ';

wherein V is $OR_4$ or hydroxy $C_{1-6}$ alkylene; provided that d'=2 when $R_5$ is piperazinyl, substituted piperazinyl, piperidyl or morpholinyl;

$R_2$ is as defined for $R_1$ with the proviso that $R_2$ is other than hydrogen when $R_1$ is hydrogen, or $R_1$ and $R_2$ taken together with the nitrogen atom to which they are attached are selected from the group consisting of;

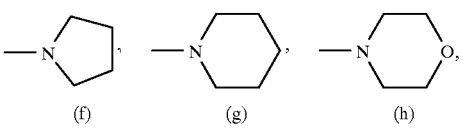

(f)    (g)    (h)

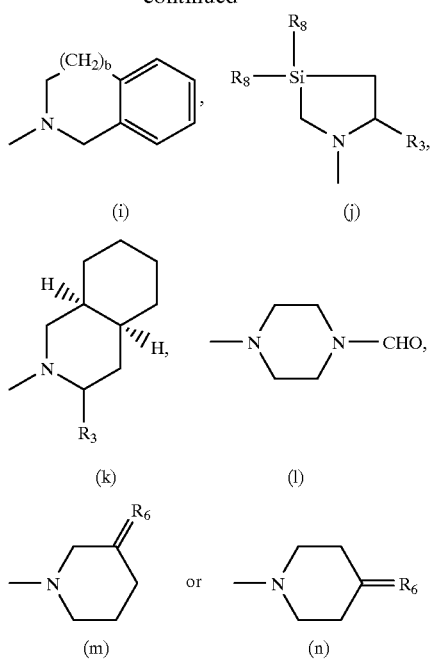

(i)    (j)    (k)    (l)    (m)    (n)

$R_3$ is $CH_2OR_4$, $C(O)NHR_4$ or CHO;
$R_4$ is hydrogen, $C_{1-6}$ alkyl, phenyl or benzyl;
$R_5$ is piperazinyl, substituted piperazinyl, piperidyl, morpholinyl, pyridyl, pyrazinyl, pyrimidinyl or phenyl, wherein substituted piperazinyl is piperazinyl substituted on one nitrogen atom thereof with CHO, $C(O)NHR_4$, $C_{1-4}$ alkyl or $CO_2R_4$;
$R_6$ is (H, OH) or =O;
$R_7$ is pyrimidyl, pyridyl, pyrazinyl or phenyl;
$R_8$ is $C_{1-6}$ allenyl, $C_{1-6}$ alkoxy, $C_{1-6}$ alkylene, hydroxy $C_{1-6}$ alkyl, $C_{1-6}$ alkyl, or OH;
a is zero, 1, 2 or 3;
b is zero or 1;
d and d' are each independently 1 or 2;
e and e' are each independently zero, 1 or 2;
f is zero or one; and
x is 1, 2, 3, or 4.

The present invention further provides a method of treating a patient suffering from a viral infection comprising administering to said patient an effective antiviral amount of a compound of formula (I).

In addition the present invention provides a method of inhibiting HIV protease in a patient in need thereof comprising administering to said patient an effective inhibitory amount of a compound of formula (I).

DETAILED DESCRIPTION OF THE INVENTION

The term "halogen", "halo" or "halide" refers to a chlorine, bromine or iodine atom. The term "stereoisomer" refers to a compound made up of the same atoms bonded by the same bonds but having different three-dimensional structures which are not interchangeable. The three dimensional structures are called configurations. The term "diastereomer" refers to those stereoisomers with more than one chiral center that are not mirror images of one another. The term "enantiomer" refers to two stereoisomers whose molecules are nonsuperimposable mirror images of one another. The term "racemic mixture" or "racemic modification" refers to a mixture of equal parts of enantiomers. The term "chiral center" refers to a carbon atom to which four different groups are attached. For amino acids, the designations L/D or R/S can be used as described in IUPAC-IUB Joint Commission on Biochemical Nomenclature, *Eur. J. Biochem.*, 138, 9–37 (1984). It is understood that the compounds of formula (I) may exist in a variety of stereoisomeric configurations. It is further understood that where the configuration of formula (1) is fixed, the maximum number of enantiomers possible for each compound is equal to $2^n$ wherein n represents the total number of chiral centers located on the compound. The minimum number of chiral centers located on formula (I) are indicated below by the * formula I

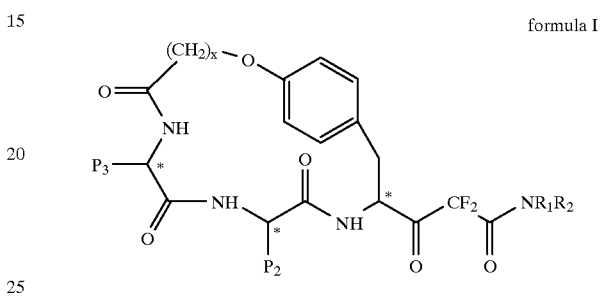

wherein the substituents are previously defined provided $P_3$ is other than hydrogen.

A compound of the invention may be in free form, e.g., amphoteric form, or in salt, e.g., acid addition or anionic salt, form. A compound in free form may be converted into a salt form in an art-known manner and vice-versa.

The pharmaceutically acceptable salts of the compounds of formula I (in the form of water, or oil-soluble or dispersible products) include the conventional non-toxic salts or the quaternary ammonium salts of these compounds, which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, paemoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The hydrates of the compounds of formula (I) are hydrated ketones compounds having the partial structure

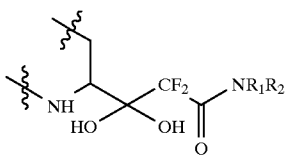

and in their end-use application are generally the active forms.

In general, as used herein, the term "alkyl" includes the straight, branched-chain and cyclized manifestations thereof unless otherwise indicated, particularly such moieties as methyl, ethyl, isopropyl, n-butyl, t-butyl, —CH₂-t-butyl, cyclopropyl, n-propyl, pentyl, cyclopentyl, n-hexyl, cyclohexyl and cyclohexylmethyl. The term "aralkyl", when used, includes those aryl moieties attached to an alkylene bridging moiety, preferably methylene or ethylene.

"Aryl" includes both carbocyclic and heterocyclic moieties of which phenyl, pyridyl, pyrimidinyl, pyrazinyl, indolyl, indazolyl, furyl and thienyl are of primary interest; these moieties being inclusive of their position isomers such as, for example, 2-, 3-, or 4-pyridyl, 2- or 3-furyl and thienyl, 1-, 2-, or 3-indolyl or the 1- and 3-indazolyl, as well as the dihydro and tetrahydro analogs of the furyl and thienyl moieties. Also included within the term "aryl" are such fused carbocyclic moieties as pentalenyl, indenyl, naphthalenyl, azulenyl, heptalenyl, acenaphthylenyl, fluorenyl, phenalenyl, phenanthrenyl, anthracenyl, acephenanthrylenyl, aceanthrylenyl, triphenylenyl, pyrenyl, chrysenyl and naphthacenyl. Also included within the term "aryl" are such other heterocyclic radicals as 2- or 3-benzo[b]thienyl, 2- or 3-naphtho[2,3-b]thienyl, 2- or 3-thianthrenyl, 2H-pyran-3-(or 4- or 5-)yl, 1-isobenzofuranyl, 2H-chromenyl-3-yl, 2- or 3-phenoxathiinyl, 2- or 3-pyrrolyl, 4- or 3-pyrazolyl, 2-pyrazinyl, 2-pyrimidinyl, 3-pyridazinyl, 2-indolizinyl, 1-isoindolyl, 4H-quinolizin-2-yl, 3-isoquinolyl, 2-quinolyl, 1-phthalazinyl, 1,8-naphthyridinyl, 2-quinoxalinyl, 2-quinazolinyl, 3-cinnolinyl, 2-pteridinyl, 4aH-carbazol-2-yl, 2-carbazolyl, β-carbolin-3-yl, 3-phenanthridinyl, 2-acridinyl, 2-perimidinyl, 1-phenazinyl, 3-isothiazolyl, 2-phenothiazinyl, 3-isoxazolyl, 2-phenoxazinyl, 3-isochromanyl, 7-chromanyl, 2-pyrrolin-3-yl, 2-imidazolidinyl, 2-imidazolin-4-yl, 2-pyrazolidinyl, 3-pyrazolin-3-yl, 2-piperidyl, 2-piperazinyl, 1-indolinyl, 1-isoindolinyl, 3-morpholinyl, benzo[b]isoquinolinyl and benzo[b]furanyl, including the position isomers thereof except that the heterocyclic moieties cannot be attached directly through their nitrogen one, two or three substituents independently selected from $C_{1-6}$ alkyl, haloalkyl, alkoxy, thioalkoxy, aminoalkylamino, dialkylamino, hydroxy, halo, mercapto, nitro, carboxaldehyde, carboxy, carboalkoxy and carboxamide.

Likewise the term "alkylene" includes straight or branched-chain moieties. Some examples of branched-chain alkylene moieties are ethylethylene, 2-methyltrimethylene, 2,2-dimethyltrimethylene, and so on. For example, $C_3$ alkylene can mean

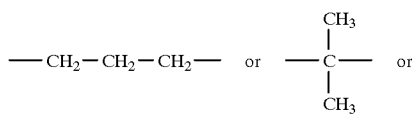

-continued

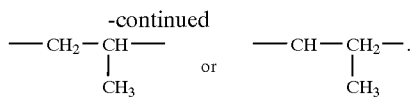

All ($C_{1-15}$) moieties are preferably ($C_{1-6}$) moieties and all ($C_{1-6}$) moieties such as $C_{1-6}$ alkyl, $C_{1-6}$ allenyl, $C_{1-6}$ alkoxy, and hydroxy $C_{1-6}$ alkyl, are more preferably $C_{1-3}$ moieties (containing 1–3 carbon atoms instead of 1–6 carbon atoms).

The fluorenylmethyloxy moiety is that moiety generally called by its abbreviation FMOC, and is the fluorenyl moiety bearing —CH₂O attached to the 9-position of the fluoroenyl moiety. Other terms defined herein are piperazinyl

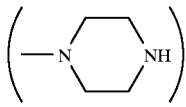

or substituted piperazinyl

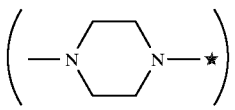

the substitution (★) occuring only at one nitrogen molecule which is not attached to the remainder of the molecule (attachment via a nitrogen atom). The substituents are one of CHO, C(O)NHR₄, $C_{1-4}$ alkyl or CO₂R₄.

More specifically, in the instance wherein P₂ is either $C_{1-6}$ alkyl or hydroxy $C_{1-6}$ alkyl, such moieties as —C(CH₃)₃, —CH(CH₃)₂, —CH(CH₃)(C₂H₅), —C(OH)(CH₃)₂ and —CH(OH)CH₃ are preferred.

Piperidyl and morpholinyl both bind to the rest of the

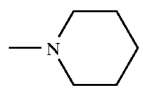 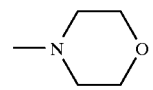

molecule via their respective nitrogen atoms while pyrimidinyl, pyridyl and pyrazinyl bind to the rest

  

of the molecule anywhere except their respective nitrogen atoms.

and the hydroxy radical is not limited to the terminal carbon atom of the alkyl moiety).

As used herein the term "Pg" refers to a protecting group. Among the classes of amino protecting groups contemplated are: (1) acyl type protecting groups such as formyl, trifluoroacetyl, phthalyl, p-toluenesulfonyl (tosyl), benzenesulfonyl, nitrophenylsulfenyl, tritylsulfenyl, and O-nitrophenoxyacetyl; (2) aromatic urethane type protecting groups such as benzyloxycarbonyl and substituted benzyloxycarbonyls such as p-chlorobenzyloxycarbonyl, p-methoxybenzyloxycarbonyl, p-nitrobenzyloxycarbonyl, p-bromobenzyloxycarbonyl, 1-(p-biphenylyl)-1-methylethoxycarbonyl, α-, α-dimethyl-3,5- dimethoxybenzyloxycarbonyl, and benzhydryloxycarbonyl; (3) aliphatic urethane protecting groups such as tert-butyloxycarbonyl (Boc), 9-fluorenylmethoxycarbonyl (FMOC), diisopropylmethoxycarbonyl, isopropyloxycarbonyl, ethoxycarbonyl, and allyloxycarbonyl; (4) cycloalkyl urethane type protecting groups such as cyclopentyloxycarbonyl, adamantyloxycarbonyl, and cyclohexyloxycarbonyl; (5) thio urethane type protecting groups such as phenylthiocarbonyl; (6) alkyl type protecting groups such as triphenylmethyl (trityl) and benzyl (Bzl); (7) trialkylsilane protecting groups such as trimethylsilane if compatible. The preferred α-amino protecting groups are tert-butyloxycarbonyl (Boc) or benzyloxycarbonyl (CBZ). The use of Boc as an α-amino protecting group for amino acids is described by Bodansky et al. in "The Practice of Peptide Synthesis", Springer-Verlag, Berlin (1984), p. 20.

Where functional groups other than the α-amino group are present, such as those that may be present on $P_3$, those groups will generally have to be protected. These functional groups may be protected by different protecting groups from those used on the a-amino groups so that one protecting group can be removed without removing the other protecting group. The selection of appropriate combinations of protective groups and reagents to selectively remove protective groups is well known in the art. For example, see M. Bodansky, "Peptide Chemistry, A Practical Textbook", Springer-Verlag (1988); J. Stewart, et al., "Solid Phase Peptide Synthesis", 2nd ed., Pierce Chemical Co. (1984).

In general the compounds of this invention may be prepared using standard chemical reactions analogously known in the art. More specifically, the preparation of compounds of structure (3) is well known in the art and described generally by Schirlin, D. and Van Dorsselaer, V. in PCT/US91/09741 published Jul. 23, 1992 with an international publication number of WO 92/12123. For example, the compounds of structure (3) and (4) which are required starting material for use in Scheme II, can be prepared as described in Scheme I. The term "Pg'" as used in Schemes I and II is a protecting group as previously defined but does not include benzyl or the aromatic urethane protecting groups described. All other substituents, unless otherwise indicated, are previously defined. The reagents and starting materials are readily available to one of ordinary skill in the art.

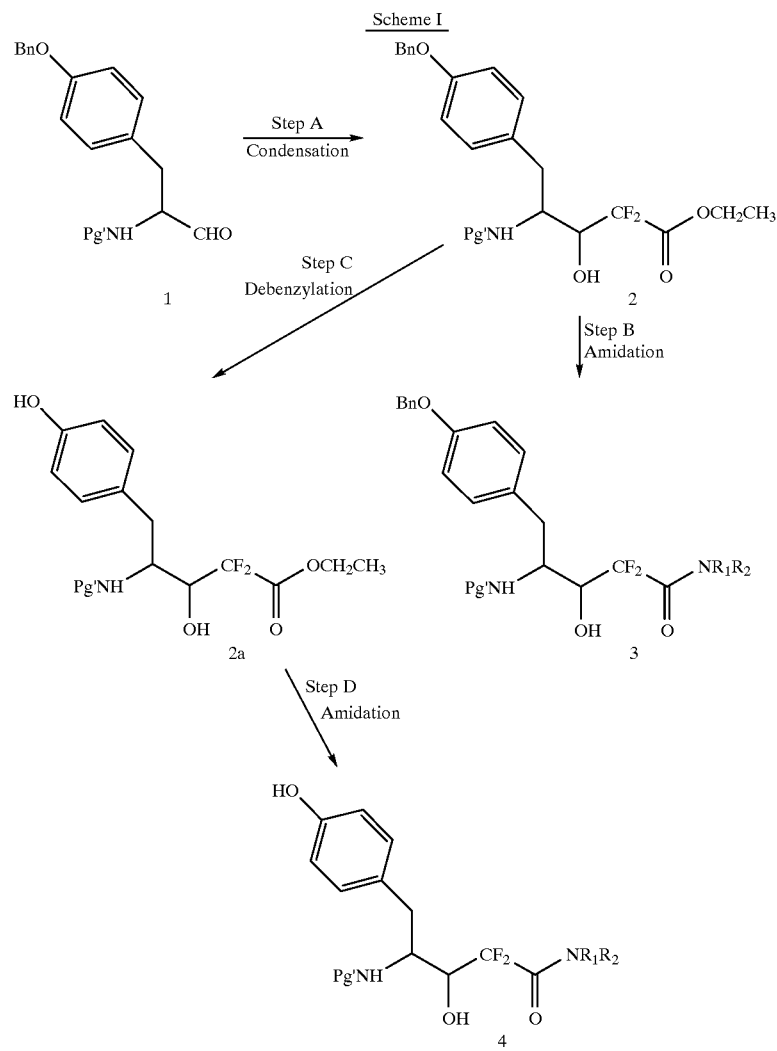

In Scheme I step A, the aldehyde (1) is subjected to a condensation reaction with an ester of bromodifluoroacetic acid, preferably the ethyl ester in the presence of zinc and in an anhydrous aprotic solvent, such as tetrahydrofuran, diethyl ether, t-butyl methyl ether and the like under a nitrogen or argon inert atmosphere. The reaction is gently heated to about 60° C. for about 1–12 hours or ultrasonicated to produce the ester described by (2). The preferred amino protecting group (Pg') on the aldehyde (1) is the tert-butyloxycarbonyl group.

Alternatively, in Scheme I step A, the condensation to produce ester (2) can be achieved in greater yields and at lower reaction temperatures utilizing the following general method. Under an inert atmosphere, such as nitrogen, the aldehyde (1) is dissolved in a suitable anhydrous organic solvent. Examples of a suitable anhydrous organic solvent are tetrahydrofuran, diethyl ether, t-butyl methyl ether and the like. The solution is cooled to approximately 0° C. To the solution is added about 0.30 equivalents of silver acetate, about 2.1 equivalents of zinc dust, and about 2 equivalents of ethyl bromodifluoroacetate. About 0.34 equivalents of diethylaluminum chloride (as a solution in toluene) is added slowly to the reaction keeping the temperature of the reaction below 12° C. The reaction is allowed to stir for 1 to 3 hours at about 0° C. and then at room temperature for 4 to 12 hours. The reaction is then cooled to about 10° C. and quenched with saturated aqueous ammonium chloride. The ester (2) is then isolated and purified by techniques well known in the art. For example a solution of sodium hydrogen tartrate is added and the reaction is allowed to warm from 10° C. to room temperature. The mixture is filtered, the solids washed with a suitable organic solvent, such as ethyl acetate and the layers of the filtrate are separated. The aqueous layer is extracted with ethyl acetate, the organic layer and extracts are combined, dried over anhydrous magnesium sulfate, filtered and concentrated. The residue if purified by flash chromatography on silica gel with a suitable eluent, such as cyclohexane/ethyl acetate to provide the ester (2).

In Scheme I step B the ester (2) is subjected to an amidation reaction to provide the amide described by structure (3). The ester (2) is dissolved in a suitable organic solvent, such as tetrahydrofuran and treated with the appropriate $R_1,R_2$-substituted amine at a temperature of from 0 to 80° C. to provide the amide (3).

Alternatively, an appropriate $R_1,R_2$-substituted amine that is protected as necessary is dissolved in a suitable organic solvent, such as dichloromethane under an inert atmosphere, such as nitrogen. An equivalent of a 2M solution of trimethylaluminum in toluene is added dropwise to the solution. After approximately 15 minutes this solution is added to approximately 0.3 equivalents of ester (2) dissolved in a suitable organic solvent, such as dichloromethane. The reaction is allowed to stir for about 15 to 24 hours at about room temperature to 40° C. The product is then isolated using techniques well known in the art. For example cold dilute aqueous hydrochloric acid and ethyl acetate is added. The organic layer is separated and washed with water, brine, dried over anhydrous magnesium sulfate, filtered and concentrated under vacuum to provide the amide (3).

Alternatively, the ester (2) may be hydrolyzed to the corresponding acid under conditions well known in the art and subsequently coupled to the appropriate $R_1,R_2$-substituted amine utilizing peptide forming coupling procedures that are well known in the art to provide the amide (3).

In Scheme I step C, the phenolic ether portion of the ester (2) is debenzylated under conditions well known in the art to provide the phenol described by structure (2a). For example, the ester (2) is dissolved in a suitable solvent mixture, such as 4.4% formic acid/methanol. A catalytic amount of palladium black is added in portions during a period of about 1 hour to 6 days until debenzylation is complete as indicated by thin layer chromatography or HPLC. The product is then isolated and purified by techniques well known in the art such as flash chromatography. For example, the reaction is filtered, the filtrate concentrated under vacuum and the residue purified by flash chromatography on silica gel utilizing a suitable eluent, such as cyclohexane/ethyl acetate to provide the phenol (2a).

In Scheme I step D, the phenol (2a) is subjected to an amidation reaction to provide the amide described by structure (4). For example, an appropriate $R_1,R_2$-substituted amine that is protected as necessary, such as O-benzyl-D-valinol is dissolved in a suitable organic solvent, such as dichloromethane under an inert atmosphere, such as nitrogen. An equivalent of a 2M solution of trimethylaluminum in toluene is added dropwise to the solution. After approximately 15 minutes this solution is added to approximately 0.3 equivalents of (2a) dissolved in a suitable organic solvent, such as dichloromethane. The reaction is allowed to stir for about 15 to 24 hours at about room temperature to 40° C. The product is then isolated using techniques well known in the art. For example cold dilute aqueous hydrochloric acid and ethyl acetate is added. The organic layer is separated and washed with water, brine, dried over anhydrous magnesium sulfate, filtered and concentrated under vacuum to provide the amide (4).

The compounds of formula (I) can be prepared as described in Scheme II. All substituents, unless otherwise indicated, are previously defined. The reagents and starting materials are readily available to one of ordinary skill in the art.

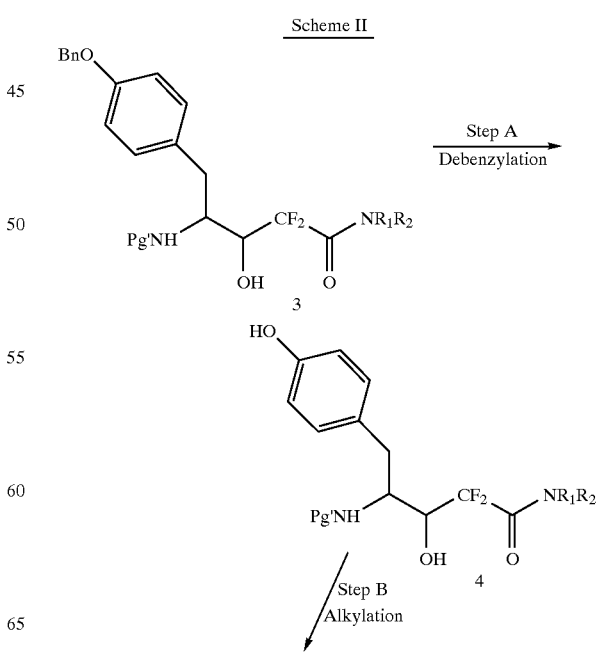

Scheme II

11
-continued

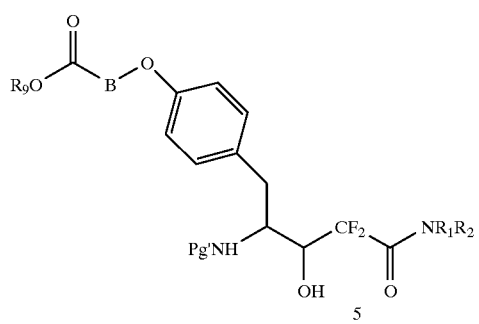
5

Step C
Deprotection

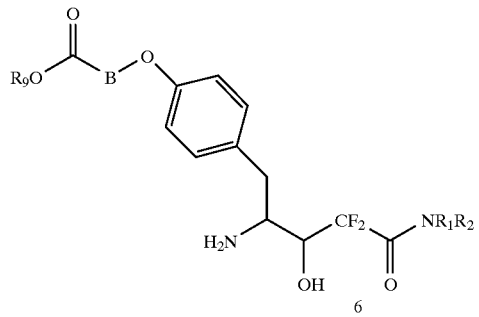
6

B = —(CH$_2$)$_x$—
R$_9$ = methyl, ethyl or propyl

Step D
Coupling Reaction with 6a

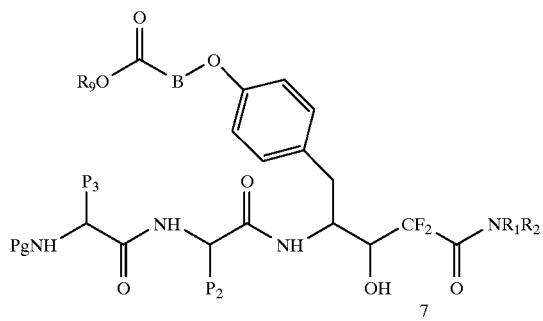
7

Step E, Hydrolysis
Step F, Esterification

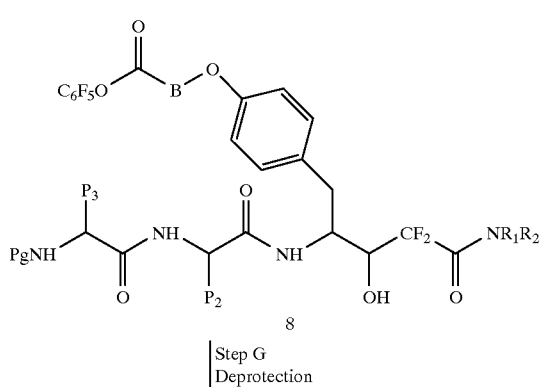
8

Step G
Deprotection

12
-continued

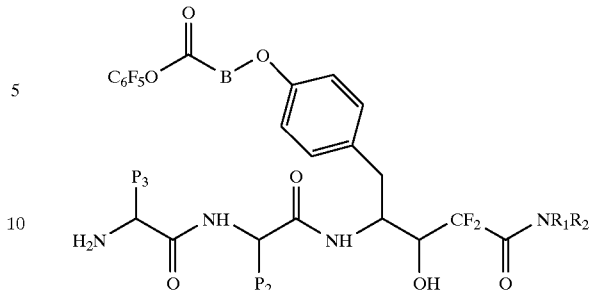
9

Step H
Cyclization

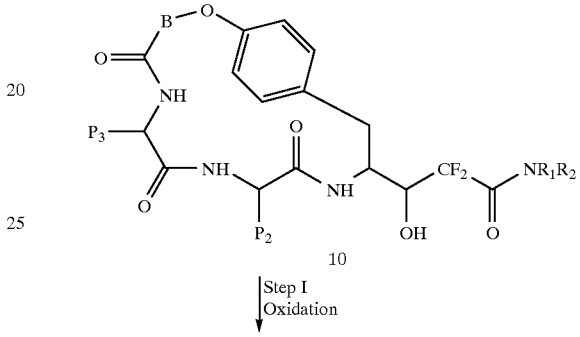
10

Step I
Oxidation

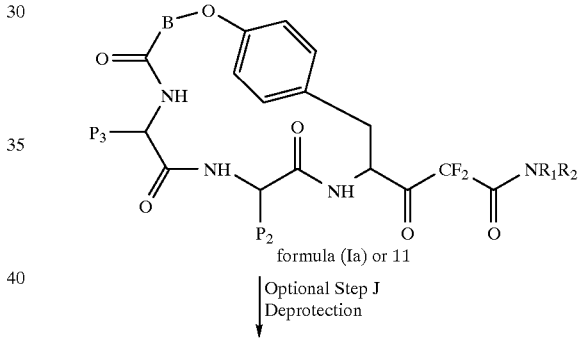
formula (Ia) or 11

Optional Step J
Deprotection

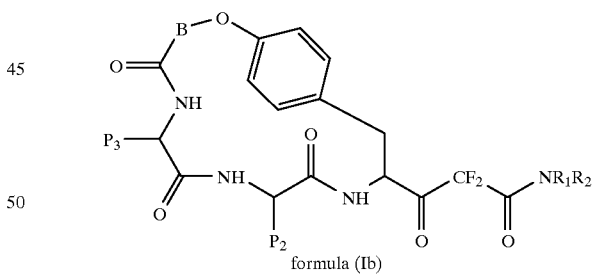
formula (Ib)

For formula (Ia), P$_3$ is not protected.
For structure (11), P$_3$ is protected as required.
Deprotection of (11) results in formula (Ib).

In Scheme II step A, the amide (3) is debenzylated to provide the phenol described by structure (4). For example, following generally the procedure of El Amin et al. *J. Org. Chem.*, 44, 3442 (1979), the amide (3) is dissolved in a suitable solvent mixture, such as 4.4% formic acid/methanol to which a catalytic amount of Pd black has been added. The reaction is stirred for about 4 to 6 hours, with additional portions of Pd black being added as needed, at intervals of about every 45 minutes until the reaction is complete. The reaction is then filtered and the filtrate is concentrated under vacuum. The residue is purified by techniques well known in the art, such as recrystallization. For example, the residue is recrystallized from a suitable solvent mixture, such as cyclohexane/ethyl acetate, to provide phenol (4).

In Scheme II step B, the phenol (4) is alkylated to provide the ether described by structure (5). For example, the phenol (4) is dissolved in a suitable organic solvent, such as acetone. Approximately 1.2 equivalents of a suitable base, such as potassium carbonate, are added followed by addition of approximately 1.15 equivalents of a suitable alkyl halide. Examples of suitable alkyl halides are ethyl bromoacetate, methyl bromoacetate, ethyl 3-bromopropionate, ethyl 3-chloropropionate, ethyl 4-bromobutyrate, ethyl 4-chlorobutyrate, ethyl 5-bromovalerate and the like. A catalytic amount of potassium iodide is then added and the reaction is stirred for 1 to 3 days. The product is isolated and purified by techniques well known in the art, such as extractive methods and recrystallization. For example, the reaction is poured into a suitable solvent mixture, such as ethyl acetate/dilute aqueous sodium chloride and the organic layer is separated. The organic layer is then washed with dilute aqueous potassium hydroxide, brine, dried over anhydrous magnesium sulfate, filtered and concentrated under vacuum. The residue is purified by recrystallization from a suitable solvent mixture, such as cyclohexane/ethyl acetate to provide the ether (5).

In Scheme II step C, the protected amine portion of ether (5) is deprotected under conditions well known in the art as described by T. H. Green, "Protective Groups in Organic Synthesis", John Wiley and Sons, 1981, Chapter 7, to provide the deprotected amine described by structure (6). For example when Pg' is t-butyloxycarbonyl, the ether (5) is treated with excess trifluoroacetic acid (TFA) and the reaction is allowed to stir for approximately 2 hours under an atmosphere of nitrogen. The reaction is then concentrated under vacuum. The residue is twice dissolved in ethyl acetate and each time concentrated under vacuum to provide the deprotected amine (6) as the TFA salt. Alternatively when Pg' is t-butyloxycarbonyl, the ether (5) may be treated with excess formic acid and allowed to stir for about 1 to 2 hours at room temperature. The deprotected amine (6) can be isolated by treatment with aqueous sodium bicarbonate and extraction with a suitable organic solvent, such as ethyl acetate. The organic extract is dried over anhydrous magnesium sulfate, filtered and concentrated under vacuum to provide the deprotected amine (6).

In Scheme II step D, the deprotected amine (6) is immediately subjected to a coupling reaction [to avoid possible lactamization of (6)] with an acid of structure (6a)

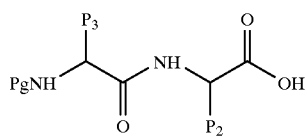

under conditions well known in the art to provide the amide described by structure (7) wherein $P_3$ is appropriately protected as required to prevent formation of undesired bonds. $P_3$ requires an appropriate protecting group when $P_3$ is —$CH_2SH$, —$CH_2OH$, —$CH(CH_3)OH$, —$CH_2(CH_2)_3NH_2$, —$CH_2(CH_2)_2NHC(=NH)NH_2$, —$CH_2CO_2H$, —$CH_2CH_2CO_2H$,

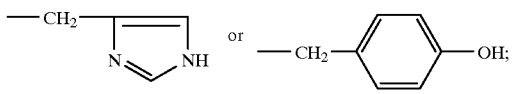

otherwise $P_3$ is not protected. The protecting groups that can be used, their selection and subsequent removal is well within the scope of the art, for example see T. H. Greene, "Protective Groups in Organic Chemistry", John Wiley & Sons, New York (1981); "The Peptides: Analysis, Synthesis, Biology", Vol. 3, Academic Press, New York (1981); M. Bodansky, "Peptide Chemistry, A Practical Textbook", Springer-Verlag (1988); and J. Stewart, et al., "Solid Phase Peptide Synthesis", 2nd ed., Pierce Chemical Co. (1984).

The selection of the appropriate coupling reaction procedure is within the skill of the art. The coupling reaction can be carried out using standard coupling procedures such as the azide method, mixed carbonic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxy-succinic imido ester) method, Woodward reagent K method, carbonyldiimidazole method, phosphorus reagents such as BOP-Cl, or oxidation-reduction methods. Some of these methods (especially the carbodiimide method) can be enhanced by adding 1-hydroxybenzotriazole. For example, the deprotected amine (6) [as the free base or the TFA salt] is dissolved in a suitable organic solvent mixture, such as methylene chloride/dimethylformamide (1:1) with stirring under an inert atmosphere, such as nitrogen. Approximately 1.06 equivalents of 1-hydroxybenzotriazole hydrate (HOBT) are added followed by addition of N-methylmorpholine [1.1 equivalents if (6) is a free base and 2.2 equivalents if (6) is the TFA salt], approximately 1.06 equivalents of (6a) and approximately 1.11 equivalents of 1-(3-dimethylaminopropyl)-3-ethylcarbodiimide hydrochloride (EDC). The reaction is allowed to stir for about 12 hours to 3 days. The product is then isolated and purified by techniques well known in the art such as extractive methods, flash chromatography and recrystallization. For example, the reaction is poured into water and the mixture is extracted with a suitable organic solvent, such as ethyl acetate. The organic extract is washed with dilute aqueous hydrochloric acid, aqueous sodium bicarbonate, brine, dried over anhydrous magnesium sulfate, filtered and concentrated under vacuum. The residue is then purified by flash chromatography utilizing a suitable eluent, such as ethyl acetate/ cyclohexane on a stationary phase of silica gel followed by crystallization from a suitable solvent mixture, such as ethyl acetate/cyclohexane to provide the amide (7).

In Scheme II steps E and F the ester portion of amide (7) is converted to the activated pentafluorophenyl ester described by structure (8). For example, the amide (7) is suspended in a suitable solvent mixture, such as methanol/ water (19:1). Approximately 1.4 equivalents of a suitable base, such as lithium hydroxide are added with stirring. The reaction is allowed to stir for about 2 to 4 hours. The reaction is then concentrated under vacuum. The resulting salt of the corresponding acid is purified by techniques well known in the art. For example, the salt is dissolved in water and washed with ether. A suitable organic solvent, such as ethyl acetate is then added to the aqueous phase and 0.1N sodium bisulfate is added with vigorous stirring until the aqueous phase become acidic. The organic layer is then separated, dried over anhydrous magnesium sulfate, filtered and concentrated under vacuum to provide the corresponding acid. The acid is then dissolved in methylene chloride. To this solution is added approximately 1.3 equivalents of pentafluorophenol and approximately 1.2 equivalents of 1-(3-dimethylaminopropyl)-3-ethylcarbodiimide hydrochloride with stirring. The reaction is allowed to stir for about 3 hours to 3 days. The product is then isolated and purified by techniques well known in the art. For example, the reaction is diluted with water and the resulting solid is then collected by filtration followed by rinsing with water and ether. It can then be recrystallized from a suitable solvent mixture, such as cyclohexane/ethyl acetate to provide the pentafluorophenyl ester (8).

In Scheme II step G, the protected amine portion of the pentafluorophenyl ester (8) is deprotected under conditions well known in the art as described by T. H. Green, "Protective Groups in Organic Synthesis", John Wiley and Sons, 1981, Chapter 7, to provide the deprotected amine described by structure (9). For example when Pg is t-butyloxycarbonyl, the pentafluorophenyl ester (8) is treated with excess 4N hydrogen chloride/dioxane with stirring. The reaction is allowed to stir for 30 minutes to 2 hours. The reaction is then concentrated under vacuum to provide the deprotected amine (9) as the hydrochloride salt.

In Scheme II step H, the deprotected amine (9) hydrochloride salt is subjected to a cyclization reaction to provide the macrocyclic alcohol described by structure (10). For example, the deprotected amine (9) is treated with a suitable base and organic solvent mixture, such as dilute aqueous sodium bicarbonate/methylene chloride. The reaction is stirred vigorously for 1 to 3 days. The product is then isolated and purified by techniques well known in the art. For example, the reaction is then filtered and the solid is rinsed with water and ether, to provide the macrocyclic alcohol (10) which can be purified by techniques well known in the art.

An alternative method for converting the amide (7) to the macrocyclic alcohol (10) can be accomplished in two steps. When Pg is an FMOC protecting group on amide (7), treatment of amide (7) with approximately 2 equivalents of a suitable base, such as lithium hydroxide will provide the acid and deprotected amine of structure (7a).

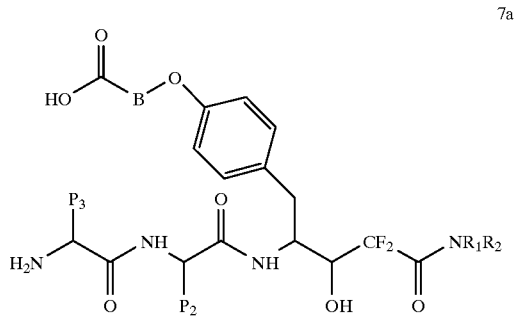

7a

Subjecting (7a) to standard coupling conditions as previously described in Scheme II, step D results in cyclization of (7a) to provide the macrocyclic alcohol (10).

In Scheme II step I, the macrocyclic alcohol (10) is oxidized under conditions well known in the art to provide the macrocyclic ketone of formula (Ia) when $P_3$ is not protected or the macrocyclic ketone of structure (11) when $P_3$ is appropriately protected. For example, the macrocyclic alcohol (10) is dissolved in a suitable organic solvent mixture, such as dimethyl sulfoxide/methylene chloride (3:1) under an atmosphere of nitrogen and cooled to approximately −15 to −17° C. Approximately 9 equivalents of oxalyl chloride are added dropwise to the solution. After about 1 hour approximately 19 equivalents of triethylamine are added to the reaction which is then allowed to slowly warm to room temperature and stir for about 17 hours. The product is then isolated and purified by techniques well known in the art, such as extractive methods, flash chromatography and recrystallization. For example, the reaction is diluted with a suitable solvent mixture, such as water/ethyl acetate. The organic layer is separated and washed with water, brine, dried over anhydrous magnesium sulfate, filtered and concentrated under vacuum. The residue is purified by flash chromatography utilizing a suitable eluent, such as ethyl acetate/methanol (19:1) and subsequent recrystallization from a suitable solvent mixture, such as ethyl acetate/ 2,2,2-trifluoroethanol to provide the macrocyclic ketone of formula (Ia) or macrocyclic ketone (11).

Alternatively the oxidation can be carried out with the Dess-Martin periodinane (i.e., 1,1,1-triacetoxy-1,1-dihydro-2,1-benzoxiodol-3(1H)-one), [see Dess Martin, *J. Org. Chem.*, 48, 4155, (1983)]. This oxidation is effected by contacting about 1 equivalent of the alcohol with 1 to 10 equivalents of periodinane (preferably greater than 5 equivalents), said reagent being in suspension in an inert solvent (e.g., methylene chloride) under an inert atmosphere (preferably nitrogen) under anhydrous conditions at 0° C. to 50° C. (preferably room temperature) and allowing the reactants to interact for about 1 to 48 hours. The desired ketone can then be isolated and purified by techniques well known in the art as described above.

In Scheme II step J, the protected portion of $P_3$ on the macrocyclic ketone (11) is deprotected under conditions well known in the art to provide the macrocyclic ketone of formula (Ib).

In Scheme III an alternative method for the preparation of compounds of formula (I) is described wherein the deprotected amine (6) prepared in Scheme II is the starting material. All other substituents, unless otherwise indicated, are previously defined. The reagents and starting materials are readily available to one of ordinary skill in the art.

Scheme III

6

Step A
Coupling Reaction with 6b

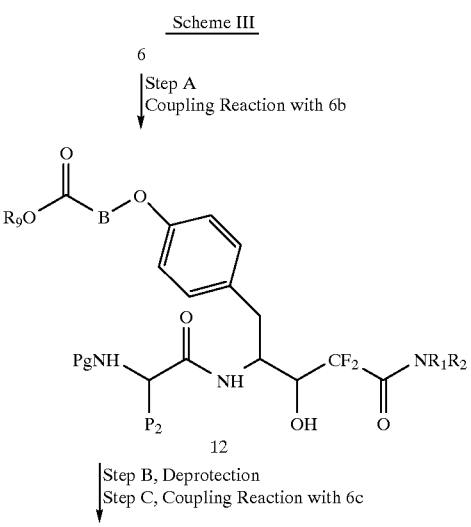

12

Step B, Deprotection
Step C, Coupling Reaction with 6c

17

-continued

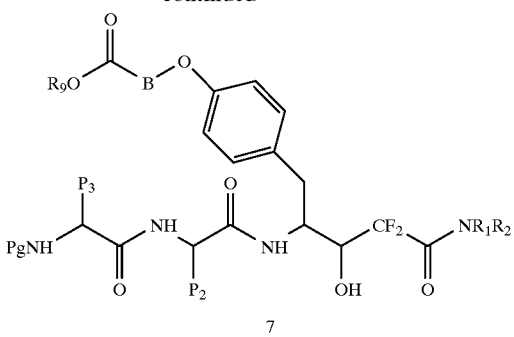

7

In Scheme III step A, the deprotected amine is subjected to a coupling reaction with an acid of structure (6b)

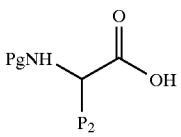

6b under the coupling conditions described previously in Scheme II step D to provide the amide of structure (12).

In Scheme III step B the amide (12) is deprotected under the conditions described in Scheme II step C to provide the deprotected amine, which is subsequently subjected to a coupling reaction with an acid of structure (6c)

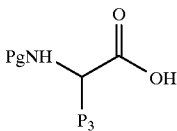

6c under the coupling conditions described previously in Scheme II step D to provide the amide of structure (7). The amide (7) is then converted to compounds of formula (I) as previously described in Scheme II.

The diastereomers of formula (I) can be separated and the enantiomers of formula (I) can be resolved utilizing techniques well known in the art such as the crystallization techniques described by Jacques, J. et al. "Enantiomers, Racemates, and Resolutions", John Wiley and Sons, Inc., 1981 or by chromatography utilizing a suitable stationary phase, such as a chiral stationary phase under HPLC (high pressure liquid chromatography) conditions or flash chromatography.

The following examples present typical syntheses as described by Schemes I, II and III. These examples are understood to be illustrative only and are not intended to limit the scope of the invention in any way. As used in the following examples, the following terms have the meanings indicated: "eq." refers to equivalents, "g" refers to grams, "mg" refers to milligrams, "mmol" refers to millimoles, "mL" refers to milliliters, "°C." refers to degrees Celsius, "TLC" refers to thin layer chromatography, "δ" refers to parts per million down field from tetramethylsilane for $^1$H NMR and "δ" refers to parts per million upfield from fluorotrichloromethane for $^{19}$F NMR.

18

EXAMPLE 1

Preparation of [9(S),12(S)]-α,α-Difluoro-9-(1-methylethyl)-β,4,7,10-tetraoxo-N-(phenylmethyl)-2-oxa-5,8,11,-triazabicyclo[12.2.2]octadeca-14,16,17-triene-12-propanamide

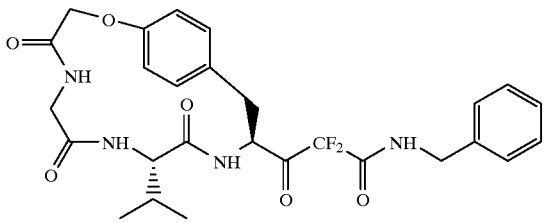

Preparation of the starting material in Scheme I, O-benzyl-N-(tert-butoxycarbonyl)-L-tyrosinal (1) [Following the procedure of Schirlin, D. and Van Dorsselaer, V. in PCT/US91/09741 published Jul. 23, 1992 with an international publication number of WO 92/12123.]

A mixture of N-tert-butoxycarbonyl-L-O-benzyltyrosine (37.1 g, 100 mmol), dicyclohexylcarbodiimide (20.6 g, 100 mmol), and N-hydroxybenzotriazole hydrate (15.3 g, 100 mmol) in anhydrous dichloromethane (350 mL) is stirred at 0° C. for 10 minutes. To this is added at 0° C., N,O-dimethylhydroxylamine hydrochloride (9.75 g, 100 mmol) and N-methylmorpholine (10.1 g, 100 mmol). The temperature is allowed to warm to room temperature and stirring is continued for 15 hours. The white precipitate is then filtered off and rinsed with dichloromethane. The filtrate is concentrated under vacuum and the residue is purified by flash chromatography (silica gel, ethyl acetate/cyclohexane, 2:8) to provide the N-tert-butoxycarbonyl-L-O-benzyltyrosine-N,O-dimethyl-hydroxamate (34.3 g) as a white solid (R$_f$= 0.36 in ethyl acetate/cyclohexane, 1:1).

The N-tert-butoxycarbonyl-L-O-benzyltyrosine-N,O-dimethyl-hydroxamate (18.2 g, 44 mmol) is dissolved in a mixture of anhydrous diethyl ether/dimethoxyethane (300 mL, 4:1) and cooled to 0° C. To this is added lithium aluminum hydride (1.82 g, 48 mmol) portionwise. The reaction is stirred at 0° C. for 1.5 hours. A 1M solution of potassium hydrogen sulfate (55 mL) is then added dropwise with stirring to the reaction. After addition is complete, the aqueous phase is decanted and extracted with ethyl acetate (2×200 mL). The combined organic layers are washed with 3N hydrochloric acid (250 mL), water (200 mL), saturated sodium bicarbonate (150 mL) and brine (200 mL). The organic layer is then dried over anhydrous magnesium sulfate, filtered and concentrated under vacuum. The residue is recrystallized from ethyl acetate/pentane to provide N-tert-butoxycarbonyl-L-O-benzyltyrosinal (13 g).

Preparation of 4-tert-butoxycarbonylamino-2,2-difluoro-3-hydroxy-5-(4-benzyloxy)phenylpentanoic acid, ethyl ester Scheme I step A; To a stirred mixture of N-tert-butoxycarbonyl-L-O-benzyltyrosinal (13.0 g, 36.6 mmol), silver acetate (1.82 g, 10.9 mmol), activated zinc dust (5.02 g, 76.8 mg-atom, washed with 3N hydrochloric acid, water, acetone and ether) and ethyl bromodifluoroacetate (14.8 g, 72.9 mmol) in anhydrous tetrahydrofuran (120 mL) at 0° C. is added diethylaluminum chloride (22.4 mL of a 1.8M solution in toluene) over 20 minutes. The temperature is kept below 12° C. during the addition. The reaction is then allowed to stir at 0° C. for 90 minutes and then at room temperature for 4 hours. The reaction is then cooled to 10° C. and quenched with saturated aqueous ammonium chloride (200 mL). A 1M solution of sodium hydrogen tartrate (200 mL) is added and the reaction is allowed to warm to room temperature. The reaction is filtered and the solids rinsed with ethyl acetate. The filtrate layers are separated and the aqueous layer is extracted with ethyl acetate. The combined organic layers are dried over anhydrous magnesium sulfate, filtered and concentrated under vacuum. The residue is purified by flash chromatography (cyclohexane/ethyl acetate, 4:1) to provide the title compound (8.34 g). The ratio of diastereomers is approximately 1:1.

Preparation of 4-tert-Butoxycarbonylamino-2,2-difluoro-3-hydroxy-5-(4-benzyloxy)phenyl-N-(phenylmethyl)pentamide Scheme I step B: To a solution of 4-tert-butoxycarbonylamino-2,2-difluoro-3-hydroxy-5-(4-benzyloxy)phenylpentanoic acid, ethyl ester (5.5 g, 11.5 mmol) in anhydrous tetrahydrofuran (50 mL) is added at 0° C., benzylamine (6.15 g, 57.5 mmol). The reaction is stirred for 3 hours at 0° C., then at room temperature for 15 hours. The reaction is then diluted with ethyl acetate (100 mL), washed with 0.1N aqueous hydrochloric acid (2×50 mL), water (50 mL), brine (50 mL) and dried over anhydrous magnesium sulfate. It is then filtered and concentrated under vacuum. The residue is recrystallized from ethyl acetate/pentane to provide the title compound (5.17 g) as a white solid.

Preparation of [3ξ,4(S)]-2,4,5-Trideoxy-4-[[(1,1-dimethylethoxy)carbonyl]-amino]-2,2-difluoro-5-[4-(hydroxy)phenyl]-N-(phenylmethyl)-L-glycero-pentonamide Scheme II step A; To a stirred suspension of Pd black (300 mg) in 4.4% HCO$_2$H/CH$_3$OH (25 mL) is added 4-tert-butoxycarbonylamino-2,2-difluoro-3-hydroxy-5-(4-benzyloxy)phenyl-N-benzyl pentamide (6:1 R/S ratio, 1.39 g, 2.57 mmol). Additional 300 mg portions of Pd black are added at 0.75 hours, 1.5 hours, and 2.25 hours. After 4.25 hours total, the catalyst is removed by filtration (CH$_3$OH rinse) and the filtrate is combined with that from a similar experiment (using 51 mg of 4-tert-butoxycarbonylamino-2, 2-difluoro-3-hydroxy-5-(4-benzyloxy)phenyl-N-benzyl pentamide) and concentrated in vacuo. Recrystallization from cyclohexane/EtOAc provides 1.10 g (92%) of the title compound (approximately 6:1 R/S ratio) as a fine ivory powder: mp 163–166° C.; IR (KBr) ν$_{max}$ 3412, 3362, 1682, 1545, 1518, 1165 cm$^{-1}$; $^1$H NMR (DMSO-d$_6$) δ 9.18 (nm, 2 H), 7.35–7.2 (m, 5 H), 6.99 (d, 2 H, J=8.2 Hz), 6.66 (d, 2 H, J=8.2 Hz), 6.19 (d, 1 H, J=9.1 Hz), 6.02 (d, 1 H, J=8.1 Hz), 4.36 (dd, 1 H, J=15.5, 6.0 Hz), 4.27 (dd, 1 H, J=15.5, 6.2 Hz), 4.0–3.87 (m, 2 H), 2.64 (m, 2 H), 1.33 (major) and 1.24 (2s, 9 H); $^{19}$F NMR (DMSO-d$_6$) δ major diastereomer: −110.82 (dd, J=255, 6 Hz), −122.39 (dd, J=255, 20 Hz), minor diastereomer: −111.05 (dd, J=255, 6 Hz), −121.78 (dd, J=255, 21 Hz); mass spectrum m/z 479 (M$^+$+29), 451 (M$^+$+1), 423, 379, 352, 351 (100), 333, 243, 91.

Preparation of [3ξ,4(S)]-2,4,5-Trideoxy-4-[[(1,1-dimethylethoxy)carbonyl]amino]-2,2-difluoro-5-[4-[2-methoxy-2-(oxo)ethoxy]phenyl]-N-(phenylmethyl)-L-glycero-pentonamide Scheme II step B; To a stirred solution of [3ξ,4(S)]-2,4,5-Trideoxy-4-[[(1,1-dimethylethoxy)carbonyl]-amino]-2,2-difluoro-5-[4-(hydroxy)phenyl]-N-(phenylmethyl)-L-glycero-pentonamide (441 mg, 0.979 mmol) in acetone (6 mL) is added powdered K$_2$CO$_3$ (165 mg, 1.20 mmol), BrCH$_2$CO$_2$CH$_3$ (110 μL, 1.16 mmol), and a catalytic amount of powdered KI. The flask is stoppered and stirring is continued for 3 days. The reaction mixture is poured into EtOAc/dilute aqueous NaCl, and the organic layer is separated and washed with dilute aqueous KOH, brine, and dried over anhydrous magnesium sulfate. The organic layer is filtered and concentrated under vacuum to provide 413 mg (81%) of the title compound as a tacky white solid. Recrystallization from cyclohexane/EtOAc provides the title compound (5.5:1 R/S ratio) as a white powder: mp 93.5–99.5° C.; IR (KBr) ν$_{max}$ 3352, 1690, 1530, 1512, 1215, 1177 cm$^{-1}$; $^1$H NMR (CDCl$_3$) δ 7.38–7.24 (m, 5H), 7.18 (nm, 1 H), 7.10 (d, 2 H, J=8.6 Hz), 6.81 (d, 2 H, J=8.6 Hz), 5.00 (d, 1 H, J=9.2 Hz), 4.72 (nm, 1 H), 4.60 and 4.58 (major) (2s in 1:5.5 ratio, 2 H), 4.50 (dd, 1 H, J=14.8, 5.7 Hz), 4.42 (dd, 1 H, J=14.8, 5.7 Hz), 4.1–3.94 (m, 2 H), 3.80 and 3.79 (major) (2s in 1:5.5 ratio, 3H), 3.0–2.8 (m, 2 H), 1.42 and 1.38 (2s, 9 H); $^{19}$F NMR (CDCl$_3$) δ minor diastereomer: −113.49 (dd, J=262, 9 Hz), major diastereomer: −115.83 (dd, J=262, 9 Hz); other F of minor diastereomer buried under this peak), −120.07 (dd, J=262, 14 Hz); mass spectrum, m/z 522 (M$^+$), 495, 451, 423 (100), 405, 243, 223, 91; [α]$^{20}$$_D$ −33.0° (c 0.81, CH$_3$OH).

Preparation of [3ξ,4(S)]-2,4,5-Trideoxy-4-[[2-[[[[(1,1-dimethylethoxy)carbonyl]amino]acetyl]amino]-3-methyl-1-oxobutyl]amino]-2,2-difluoro-5-[4-[2-methoxy-2-(oxo)ethoxy]phenyl]-N-(phenylmethyl)-L-glycero-pentonamide Scheme II steps C and D; A solution of [3ξ,4(S)]-2,4,5-trideoxy-4-[[(1,1-dimethylethoxy)carbonyl]amino]-2,2-difluoro-5-[4-[2-methoxy-2-(oxo)ethoxy]phenyl]-N-(phenylmethyl)-L-glycero-pentonamide (413 mg, 0.790 mmol) in trifluoroacetic acid (TFA) (4 mL) is allowed to stir under nitrogen for 2 hours. The solution is concentrated in vacuo and the residue is twice dissolved in EtOAc and concentrated again. The resulting TFA salt is dissolved in 1:1 CH$_2$Cl$_2$/DMF (3 mL) with stirring under nitrogen and 1-hydroxybenzotriazole hydrate (HOBT) (128 mg, 0.84 mmol), N-methylmorpholine (NMM) (190 μL, 1.73 mmol), Boc-gly-val-OH (230 mg, 0.84 mmol, prepared by reaction of commercially available gly-val-OH with di-t-butyldicarbonate under standard conditions), and EDC (168 mg, 0.88 mmol) are added in that order. After 3 days, the mixture is poured into water and extracted twice with EtOAc. The combined extracts are washed with dilute aqueous HCl, NaHCO$_3$, and brine, and dried over anhydrous magnesium sulfate. The organic layer is concentrated under vacuum to provide 549 mg of gummy solid which is purified by flash chromatography (3:1 EtOAc/cyclohexane) to provide the title compound (443 mg) as a white solid. Recrystallization from EtOAc/cyclohexane provides the title compound (6.6:1 R/S ratio) as white granules: mp 161–166° C.; IR (KBr) ν$_{max}$ 3395, 3298, 1684, 1647, 1537, 1514, 1206, 1179 cm$^{-1}$; $^1$H NMR (DMSO-d$_6$) δ 9.14 (nm, 1 H), 7.76 (d, 1 H, J=8.7 Hz), 7.55 (d, 1 H, J=8.8 Hz), 7.35–7.2 (m, 5 H), 7.13 (d, 2 H, J=8.6 Hz), 7.09 (m, 1 H), 6.84 (d, 2 H, J=8.6 Hz), 6.32 (d, 1 H, J=7.6 Hz), 4.75 (major) and 4.73 (2s in 6.6:1 ratio, 2 H), 4.4–3.93 (m, 5 H), 3.69 (major) and 3.69 (2s, 3 H), 3.56 (inner peaks of apparent AB, 2 H), 2.75 (dd, 1 H, J=13.4, 8.1 Hz), 2.62 (dd, 1 H, J=13.4, 6.0 Hz), 1.98 (m, 1 H), 1.38 (major) and 1.36 (2s, 9 H), 0.80 (d, 3 H, J=6.7 Hz), 0.76 (d, 3 H, J=6.6 Hz); $^{19}$F NMR (CDCl$_3$) δ major diastereomer: −110.67 (d, J=255 Hz), −122.89 (dd, J=255, 20 Hz), minor diastereomer: −110.93 (d, J=257 Hz), −122.29 (dd, J=257, 20 Hz); mass spectrum, m/z 707 (M$^+$+29), 679 (M$^+$+1), 623, 579, 405 (100).

The pure [3(S),4(S)] title compound was obtained as a white powder after recrystallization from CH$_3$OH/butanone/ EtOAc: mp 209–211° C.; IR (KBr) ν$_{max}$ 3306, 1680, 1653, 1537, 1514, 1211, 1179 cm$^{-1}$; $^1$H NMR (DMSO-d$_6$) δ (major rotamer) 9.25 (t, 1 H, J=6.0 Hz), 7.94 (d with upfield shoulder, 1 H, J=8.6 Hz), 7.41–7.21 (m, 6 H), 7.08–7.00 (m, 3 H), 6.77 (d, 2 H, J=8.4 Hz), 6.25 (bs, 1 H), 4.72 (s, 2 H), 4.36 (m, 2 H), 4.24–3.95 (m, 3 H), 3.69 (s, 3 H), 3.53 (inner peaks of apparent AB, not integrated), 2.94–2.81 (m, 1 H), 2.61 (dd, 1 H, J=14.1, 10.7 Hz), 1.87 (m, 1 H), 1.38 (2s, 9 H), 0.72 (d, 3 H, J=7.0 Hz), 0.69 (d, 3 H, J=7.0 Hz); $^{19}$F NMR (CDCl$_3$) δ −109.90 (dd, J=252, 7 Hz), −119.82 (dd, J=252, 19 Hz) [shoulders present at δ −109.8 and −119.9]; FAB mass spectrum, m/z 679 (M$^+$+1), 579, 423, 405, 358, 307 (100), 289.

Preparation of [3ξ,4(S)]-2,4,5-Trideoxy-4-[[2-[[[[(1, 1-dimethylethoxy)carbonyl]amino]acetyl]amino]-3-methyl-1-oxobutyl]amino]-2,2-difluoro-5-[4-[2-oxo-2-(pentafluorophenoxy)ethoxy]phenyl]-N-(phenylmethyl)-L-glycero-pentonamide Scheme II, steps E and F; To a stirred suspension of [3ξ,4(S)]-2,4,5-trideoxy-4-[[2-[[[[(1,1-dimethylethoxy) carbonyl]amino]acetyl]amino]-3-methyl-1-oxobutyl] amino]-2,2-difluoro-5-[4-[2-methoxy-2-(oxo)ethoxy] phenyl]-N-(phenylmethyl)-L-glycero-pentonamide (400 mg, 0.589 mmol) in 19:1 CH$_3$OH/H$_2$O (20 mL) is added LiOH.H$_2$O (29 mg, 0.69 mmol). After 2 hours, additional LiOH.H$_2$O (5 mg, 0.81 mmol total) is added, and after an additional 2 hours, the solution is concentrated in vacuo. The residue is dissolved in water; the aqueous solution is washed with ether, is covered with EtOAc, and is acidified with vigorous stirring by the addition of 0.1 N NaHSO$_4$ (10 mL). The organic layer is separated, and the aqueous layer is extracted with a second portion of EtOAc. The combined organic layers are washed with brine and dried over anhydrous magnesium sulfate. The organic layer is concentrated under vacuum to provide 407 mg (392 mg theory) of the corresponding acid, which is dissolved in CH$_2$Cl$_2$ (5 mL) and DMSO-d$_6$ (1 mL). To this stirred solution under nitrogen is added C$_6$F$_5$OH (139 mg, 0.755 mmol) and EDC (140 mg, 0.73 mmol). After 3 days the mixture is diluted with water and filtered, washing the ivory solid with water and ether. Attempted recrystallization from CF$_3$CH$_2$OH/EtOAc results in partial transesterification to the trifluoroethyl ester. The mixture can be saponified and reesterified to provide 394 mg of crude title compound. In a similar experiment recrystallization from CF$_3$CH$_2$OH/EtOAc (filtering the hot solution through filter aid) also provides pure title compound as fine white matted crystals: mp 202–204° C.; IR (KBr) ν$_{max}$ 3389, 2974, 1684, 1653, 1522, 1173, 1121, 1080, 997 cm$^{-1}$; $^1$H NMR (DMSO-d$_6$) δ 9.14 (m, 1 H), 7.77 (d, 1 H, J 9 Hz), 7.54 (d, 1 H, J=8.9 Hz), 7.35–7.22 (m, 5 H), 7.17 (d, 2 H, J=8.7 Hz), 7.08 (nm, 1 H), 6.95 (d, 2 H, J=8.7 Hz), 6.33 (d, 1 H, J=7.6 Hz), 5.34 (s, 2 H), 4.4–4.18 (m, 4 H), 4.08–3.95 (m, 1 H), 3.55 (nm, 2 H), 2.8–2.58 (m, 2 H), 1.97 (m, 1 H), 1.38 (major) and 1.36 (2s, 9 H total), 0.80 (d, 3 H, J=6.6 Hz), 0.76 (d, 3 H, J=6.7 Hz); $^{19}$F NMR (DMSO-d$_6$) δ −110.69 (d, J=256 Hz), −122.89 (dd, J=255, 20 Hz), −152.37 (d, J=20 Hz), −156.95 (t, J=23 Hz), −161.75 (dd, J=23, 20 Hz); mass spectrum, m/z 831 (M$^+$+1), 775, 731. The [3(S), 4(S)]-title compound is not isolated, but is converted directly to the macrocyclic alcohol.

Preparation of [(9S),12(S)]-α,α-Difluoro-β-hydroxy-9-(1-methylethyl)-4,7,10-trioxo-N-(phenylmethyl)-2-oxa-5,8,11-triazabicyclo[12.2.2] octadeca-14,16,17-triene-12-propanamide Scheme II, steps G and H; [3ξ,4(S)]-2,4,5-Trideoxy-4-[[2-[[[[(1,1-dimethylethoxy)carbonyl]amino]acetyl]amino]-3-methyl-1-oxobutyl]amino]-2,2-difluoro-5-[4-[2-oxo-2-(pentafluorophenoxy)ethoxy]phenyl]-N-(phenylmethyl)-L-glycero-pentonamide (494 mg, 0.595 mmol) is suspended in 4 N HCl/dioxane (16 mL) with stirring. After 2 hours, a clear gel forms. The solvent and HCl are removed in vacuo and the residual solid is suspended in dilute aqueous NaHCO$_3$/ CH$_2$Cl$_2$ with vigorous stirring for 3 days. The mixture is filtered, and the ivory solids are washed with water and ether. Hot EtOAc is added along with just enough CF$_3$CH$_2$OH to dissolve most of the solids; filtration through filter aid and concentration under vacuum provides 256 mg of title compound. In a similar experiment the filtrate is concentrated and diluted with hot EtOAc to obtain the (R)-alcohol of the title compound as fine white granules: mp >255° C.; IR (KBr) ν$_{max}$ 3412, 3318, 1663, 1537, 1514 cm$^{-1}$; $^1$H NMR (DMSO-d$_6$) δ 9.17 (m, 1 H), 7.90 (m, 1 H), 7.64 (m, 1 H), 7.37–7.2 (m, 5 H), 7.11 (m, 1 H), 7.01 (m, 1 H), 6.93 (m, 1 H), 6.81 (m, 1 H), 6.46 (m, 1 H), 6.14 (dd, 1 H, J=7.4, 0.9 Hz), 4.60 ("d", 1 H, J=15 Hz), 4.5–4.1 (m, 6 H), 3.96 (m, 1 H), 3.72–3.54 (2m, 2 H), 2.76 (m, 1 H), 1.78 (m, 1 H), 0.77–0.71 (m, 6 H); $^{19}$F NMR (DMSO-d$_6$) δ major conformer (85%) −109.96 (dd, J=256, 5 Hz), −122.71 (dd, J=256, 20 Hz), minor conformer (15%) −110.45 (d, trace impurity),−122.3(m, trace impurity); mass spectrum, m/z 547 (M$^+$+1).

In the preparation of title compound, the crude material from the deprotection/cyclization is triturated with several portions of boiling CH$_3$OH to dissolve the (S)-alcohol of the title compound and remove some insoluble polymeric material. The solvent is removed under vacuum and the residue is triturated with several portions of boiling CF$_3$CH$_2$OH. The insoluble beige powder is the (S)-alcohol of the title compound: IR (KBr) ν$_{max}$ 3401, 3298, 1678, 1643, 1543, 1514 cm$^{-1}$; $^{19}$F NMR (DMSO-d$_6$) δ −108.94 (dd, J=253, 6 Hz), −121.27 (dd, J=253, 20 Hz); mass spectrum, m/z 575 (M$^+$+29), 547 (M$^+$+1), 113 (100); exact ass calcd for C$_{27}$H$_{33}$F$_2$N$_4$O$_6$ 547.2368, found 547.2344. The (S)-alcohol of the title compound is not carried on in this particular experiment; however, it can be subjected to the following reactions in a manner analogous to the (R)-alcohol to provide the ultimate title compound. In addition a mixture of the (R) and (S)-alcohols can also be subjected to the following reactions in an analgous manner to provide the ultimate final product. The asymmetric center is destroyed in the final oxidation of this alcohol to provide the ketone, thus separation of these alcohols is not critical.

Preparation of [(9S),12(S)]-α,α-Difluoro-9-(1-methylethyl)-β,4,7,10-tetraoxo-N-(phenylmethyl)-2-oxa-5,8,11-triazabicyclo[12.2.2]octadeca-14,16,17-triene-12-propanamide Scheme II, step I; [(9S),12(S)]-α,α-Difluoro-β-hydroxy-9-(1-methylethyl)-4,7,10-trioxo-N-(phenylmethyl)-2-oxa-5, 8,11-triazabicyclo[12.2.2]octadeca-14,16,17-triene-12 -propanamide (240 mg, 0.439 mmol) is dissolved in DMSO (6 mL) by heating at 60° C. under nitrogen with vigorous stirring. Upon cooling, the solution is diluted with CH$_2$Cl$_2$ (2 mL) and cooled to −15 to −17° C. in an ice/CH$_3$OH bath. 2 M oxalyl chloride/CH$_2$Cl$_2$ (2.0 mL) is added dropwise to provide a thin slurry. After 1 hour, Et$_3$N (1.15 mL, 8.25 mmol) is added and the mixture is slowly allowed to warm to room temperature. After 17 hours, the mixture is diluted with water/EtOAc. The organic layer is separated and the aqueous layer is extracted with a second portion of EtOAc; some insoluble white solid (18 mg) is present which is starting material. The combined organic extracts are washed three times with water, brine, and dried over anhydrous magnesium sulfate. The organic layer is then filtered and concentrated under vacuum. The crude white residue (101 mg) is purified by flash chromatography (19:1 EtOAc/CH$_3$OH) to provide 27 mg of a nonpolar oil (discarded) and 70 mg of a white solid/gel. Repeated recrystallizations from EtOAc/CF$_3$CH$_2$OH gave a white gel which is washed with 19:1 CH$_2$Cl$_2$/CH$_3$OH to give 17 mg of the title compound as a light beige powder, a mixture consisting primarily of the minor [9(S),12(R)] diastereomer, but also containing the [9(S),12(S)] diastereomer, as well as a presumed hydrate of the [9(S),12(R)] diastereomer. The insoluble gel was recrystallized further from the same solvent mixture to give 5 mg of the [9(S),12(S)] diasteromer as fine, light beige granules. For the mixture: IR (KBr) $v_{max}$ 3420, 1669, 1530, 1514 cm$^{-1}$; $^{19}$F NMR (DMSO-d$_6$) δ [9(S),12(R)] diastereomer: −105.89 (d, J=263 Hz), −111.90 (d, J=263 Hz); [9(S),12(S)] diastereomer: −109.13 (d, J=274 Hz) −111.77 (d, J=274 Hz); presumed hydrate of the [9(S),12(R)] diastereomer: −105.62 (d, J=271 Hz), −123.35 (d, J=271 Hz) (70:18:12 mixture, respectively); mass spectrum (CI, 70 eV), m/z 573 (M$^+$+29), 571, 545 (M$^+$+1), 308, 268, 250 (100), 190, 91; exact mass calcd for C$_{27}$H$_{30}$F$_2$N$_4$O$_6$ 545.2212, found 545.2239. For the [9(S),12(S)] diastereomer: IR (KBr) $v_{max}$ 3418, 1667, 1535, 1514 cm$^{-1}$; $^{19}$F NMR (DMSO-d$_6$) δ −109.12 (d, J=274 Hz); −111.77 (d, J=274 Hz), plus minor impurities; mass spectrum (CI, 70 eV), m/z 573 (M$^+$+29), 545 (M$^+$+1), 308 (100), 91; exact mass calcd for C$_{27}$H$_{30}$F$_2$N$_4$O$_6$ 545.2212, found 545.2230.

EXAMPLE 2

Preparation of [(9S),12(S)]-α,α-Difluoro-9-(1-methylethyl)-β,4,7,10-tetraoxo-N-[2-methyl-1-[(phenylmethoxy)methyl]propyl]-2-oxa-5,8,11,-triazabicyclo[12.2.2]octadeca-14,16,17-triene-12-propanamide

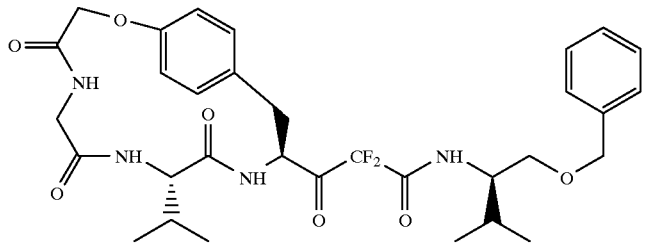

Preparation of the starting material O-benzyl-D-valinol required for the following reaction A solution of D-valinol (5.1 g, 49.4 mmol) and di-tert-butyldicarbonate (10.9 g, 52 mmol) in methanol (60 mL) is stirred for 17 hours at room temperature. After concentration under vacuum, the residue is purified by flash chromatography (silica gel, ethyl acetate/petroleum ether: 3/7, R$_f$: 0.37) to provide N-tert-butoxycarbonyl-D-valinol in quantitative yield (10.07 g, colorless oil).

To a solution of N-tert-butoxycarbonyl-D-valinol (10 g, 49.3 mmol) and benzylbromide (5.86 mL, 49.3 mmol) in anhydrous dimethyl formamide (50 mL) is added at −5° C. and under nitrogen, potassium-tert-butoxide (11.06 g, 98.6 mmol) as a solid, portionwise, an in such a way that the internal temperature does not exceed +5° C. The reaction mixture is stirred for 2 hours at 0° C., diluted with ethyl acetate (2×300 mL), extracted with a 1N solution of potassium hydrogen sulfate (50 mL) and water (250 mL) and is washed twice with water (2×200 mL). After drying of the organic phase over anhydrous sodium sulfate, filtration and concentration under vacuum, the oil is purified by flash chromatography (silica gel, ethyl acetate/petroleum ether: 1/9, Rf: 0.42) to provide N-tert-butoxycarbonyl-O-benzyl-D-valinol as a colorless oil (9.95 g, 69% yield).

A solution of N-tert-butoxycarbonyl-O-benzyl-D-valinol (9.95 g, 34 mmol) in formic acid (50 mL) is stirred for 4 hours at room temperature. After removal of the formic acid under vacuum, the sticky residue is dissolved in water (100 mL), neutralized with a saturated solution of sodium bicarbonate (100 mL) and the organic material is extracted twice with ethyl acetate (2×200 mL). The organic phases are washed until neutral with water (2×200 mL) and the combined organic layers are dried over anhydrous sodium sulfate. Filtration and concentration under vacuum provides O-benzyl-D-valinol as a slightly yellowish oil (5.20 g, 79%).

Scheme I step C; Combine 4-tert-butoxycarbonylamino-2,2-difluoro-3-hydroxy-5-(4-benzyloxy)phenylpentanoic acid, ethyl ester (756 mg, 1.58 mmol, prepared in example 1, Scheme I step A) and 4.4% formic acid/methanol (9 mL) under an atmosphere of nitrogen. Add palladium black (171 mg) and stir for 1 hour. After 1 hour, then 4 hours and finally after 2 days, add respectively additional amounts of palladium black (80 mg, 378 mg and 111 mg). After 6 days filter the reaction and concentrate the filtrate under vacuum. Purify the residue by flash chromatography (silica gel, cyclohexane/ethyl acetate, 2:1 followed by 1:1) to provide the debenzylated product (380 mg, 58%) as a light yellow foam.

Scheme I step D; Add trimethylaluminum (1.55 mL of a 2M solution in toluene) dropwise to a solution of O-benzyl-D-valinol (600 mg, 3.11 mmol, prepared above) in dry dichloromethane (1 mL) under an atmosphere of nitrogen. Stir the reaction for 15 minutes and add a solution of the above prepared debenzylated product (380 mg, 0.976 mmol) in dry dichloromethane (1 mL). Add an additional amount of dichloromethane (3 mL) and stir for 19 hours at room temperature. Add dry tetrahydrofuran (5 mL) and stir for 3 hours. Partition the reaction between cold dilute aqueous hydrochloric acid and ethyl acetate. Separate the layers and wash the organic layer with water and brine. Dry the organic layer over anhydrous magnesium sulfate, filter and concentrate under vacuum. Subject the residue to a second amidation reaction under identical conditions as above to drive the reaction further toward completion. Work up the second reaction in a manner analogous to the first reaction. Purify the residue by flash chromatography (silica gel, cyclohexane/ethyl acetate, 5:3) to provide impure product (351 mg) which is contaminated with ester starting material. To purify the product further dissolve the above impure product in methanol (10 mL) and water (0.5 mL). Add lithium hydroxide.H$_2$O (48 mg) and stir for 3 hours. Then partially concentrate the reaction under vacuum, dilute with water, add ether and cold dilute aqueous hydrochloric acid. Separate the layers and extract the aqueous with ether. Combine the organic layer and extract and wash with water, aqueous potassium carbonate (2×) and brine. Dry the organic layers over anhydrous magnesium sulfate, filter and concentrate under vacuum to provide the amide (3.5:1 R/S at the hydroxyl) (266 mg, 51 %): $^{19}$F NMR (CDCl$_3$) δ (R) diastereomer: −115.57 (dd, J=260, 8 Hz), −121.65 (dd, J=260, 17 Hz); (S) diastereomer: −112.00 (d, J=266 Hz), −120.7 (dd, J=266, 18 Hz).

Scheme II step B; Combine the above prepare amide (266 mg, 0.496 mmol) with powdered potassium carbonate (80 mg, 0.58 mmol) in acetone (3 mL) under an atmosphere of nitrogen. Add dropwise to the stirring mixture methyl bromoacetate (56 μL, 0.59 mmol). Stir the reaction for 3 days. The product is worked-up in a manner analogous to that described in example 1, Scheme II step B. If residual starting material remains subject the impure product to the same alkylating conditions as described above with catalytic amount of potassium iodide added. Stir for 24 hours. Isolate the product by the work up procedure described previously. Purify by flash chromatography (silica gel, cyclohexane/ethyl acetate, 5:3) to provide the desired alkylated product (143 mg, 47%, 5:1 R/S at the hydroxyl): $^{19}$F NMR (CDCl$_3$) δ (R) diastereomer: −155.53 (dd, J=261, 7 Hz), −122.06 (dd, J=261, 17 Hz); (S) diastereomer: −113.83 (d, J=256 Hz), −127.56 (dd, J=256, 19 Hz).

Scheme II step C; Combine the above prepared alkylated product (143 mg, 0.235 mmol) with formic acid (3 mL, 96%) and stir the reaction at room temperature for 1.5 hours. Concentrate the reaction under vacuum and partition the residue between ethyl acetate and dilute aqueous sodium bicarbonate. Separate the organic layer and wash with water (2×). Concentrate under vacuum to provide the deprotected amine (114 mg, 95%).

Scheme II step D; Combine the above deprotected amine (114 mg), 1-hydroxybenzotriazole hydrate (38 mg, 0.25 mmol), 1-(3-dimethylaminopropyl)-3-ethylcarbodiimide hydrochloride (55 mg, 0.29 mmol), N-methylmorpholine (28 μL, 0.25 mmol) and Boc.gly.val (69 mg, 0.25 mmol) in dichloromethane/dimethylformamide at 0° C. The reaction is allowed to warm to room temperature and after 16 hours, the mixture is poured into water and extracted twice with EtOAc. The combined extracts are washed with dilute aqueous HCl, NaHCO$_3$, and brine, and dried over anhydrous magnesium sulfate. The organic layer is filtered and concentrated under vacuum. The residue is purified by flash chromatography (silica gel, ethyl acetate/cyclohexane, 70:30) followed by recrystallization from cyclohexane/ethyl acetate to provide the desired amide (137 mg, 76%) as fine white granules: mp 161.5–163.5° C.; IR (KBr) ν$_{max}$ 1696, 1653, 1514 cm$^{-1}$; $^1$H NMR (CDCl$_3$) δ 7.37–7.26 (m, 5H), 7.11(d, 2H, J=8.6 Hz), 6.9 (m, 2H), 6.78 (d, 2H, J=8.6 Hz), 6.62 (bd, 1H), 5.44 (m, 1H), 4.86 (bs, 1H), 4.60 (s, 2H), 4.54 (d, 1H, J=11.9 Hz), 4.46 (d, 1H, J=11.9 Hz), 4.4–4.3 (m, 1H), 4.2–4.03 (m, 2H), 3.9–3.75 (m, 2H), 3.81 (s, 3H), 3.67–3.59 (m, 2H), 3.49 (dd, 1H, J=10.0, 3.8 Hz), 2.89 (apparent doublet, 2H), 2.15–1.92 (m, 2H), 1.45 (s, 9H), 0.94 (d, 6H, J=6.75 Hz), 0.88 (d, 3H, J=6.7 Hz), 0.84 (d, 3H, J=6.6 Hz); $^{19}$F NMR (CDCl$_3$) δ −116.78 (d, J=258 Hz), −120.16 (dd, J=258, 9 Hz); mass spectrum (FAB), m/z 765 (M$^+$+1), 709, 665, 509(100), 419, 382.

Scheme II steps E and F; Combine the above prepared amide (137 mg, 0.179 mmol) with lithium hydroxide .H$_2$O (12 mg, 0.29 mmol) in methanol (4.5 mL) and water (0.5 mL). Stir the reaction for 3 hours. The reaction is then concentrated under vacuum. The residue is dissolved in water. The aqueous solution is washed with ether, is covered with EtOAc, and is acidified with vigorous stirring by the addition of 0.1 N NaHSO$_4$. The organic layer is separated, and the aqueous layer is extracted with a second portion of EtOAc. The combined organic layers are washed with brine and dried over anhydrous magnesium sulfate. The organic layer is concentrated under vacuum to provide the corresponding acid which is dissolved in CH$_2$Cl$_2$ (3 mL). To this stirred solution under nitrogen is added C$_6$F$_5$OH (40 μL, 0.35 mmol) and EDC (45 mg, 0.23 mmol). After 1 day the mixture is diluted with water and filtered to provide the desired pentafluorophenyl ester (161 mg, 98%) as fine white granules. Recrystallization from cyclohexane/ethyl acetate provides the pentafluorophenyl ester; mp 139.5–143° C.; IR (KBr) ν$_{max}$ 3416, 3376, 3312, 1697, 1661, 1522, 1171, 1121, 1078, 997 cm$^{-1}$; $^1$H NMR (CDCl$_3$) δ 7.39–7.25 (m, 5H), 7.16 (d, 2H, J=8.5 Hz), 6.94–6.78 (m, 2H), 6.86 (d, 2H, J=8.6 Hz), 6.57 (d, 1H, J=9.0 Hz), 5.24 (nm, 1H), 4.96 (s, 2H), 4.74 (nm, 1H), 4.54 (d, 1H, J=11.9 Hz), 4.45 (d, 1H, J=11.9 Hz), 4.30 (m, 1H), 4.19–3.99 (m, 2H), 3.9–3.79 (m, 1H), 3.73 (dd, 1H, J=18.2, 5.6 Hz), 3.64 (m, 2H), 3.49 (m, 1H), 2.91 (apparent narrow d, 2H), 2.11 (m, 1H), 1.99 (m, 1H), 1.45 (s, 9H), 0.94 (d, 3H, J=6.7 Hz), 0.93 (d, 3H, J=6.75 Hz), 0.89 (d, 3H, J=6.75 Hz), 0.84 (d, 3H, J=6.95 Hz); $^{19}$F NMR (CDCl$_3$) δ −116.65 (d, 1F, J=259 Hz), −120.28 (dd, 1F, J=262, 9 Hz), −152.68 (d, 2F, J=18 Hz), −157.39 (t, 1F, J=22 Hz), −162.13 (dd, 2F, J=22, 18 Hz); mass spectrum (FAB), m/z 917(M$^+$+1), 861, 817, 661(100), 571, 534, 360, 331, 173.

Scheme II steps G and H; Combine the above prepared pentafluorophenyl ester (155 mg, 0.169 mmol) with formic acid (4.5 mL, 96%) and stir for 2 hours. Concentrate the reaction under vacuum. Add methylene chloride (50 mL) and saturated sodium bicarbonate (50 mL). Stir the reaction for 3 days. Add ethyl acetate and filter through fine fritted glass filter. Wash the gel with water. Separate the organic layer in the filtrate, wash with water (3×) and concentrate under vacuum. Purify the residue by flash chromatography (silica gel, 95% methanol/ethyl acetate) to provide the macrocyclic alcohol (9 mg, 8% (R) diastereomer at the hydroxyl) as a waxy white solid: $^1$H NMR (CD$_3$OD) δ 7.42–7.27 (m, 5H), 7.23 (m, 1H), 7.00 (m, 1H), 6.91 (m, 1H), 6.58 (m, 1H), 4.71 (d, 1H, J=16.0 Hz), 4.65–4.5 (m, 1H), 4.59 (d,1H, J=12.1 Hz), 4.56 (d, 1H, J=15.6 Hz), 4.54 (d, 1H, J=12.1 Hz), 4.24 (m, 1H), 4.08–4.01 (m, 2H), 3.94 (narrow m, 1H), 3.70–3.57 (m, 3H), 2.93 (dd, 1H, J=13.2, 3.4 Hz), 2.73 (dd, 1H, J=13.1, 12.5 Hz), 2.01 (m, 1H), 1.89 (m, 1H), 1.01 (d, 3H, J=6.2 Hz), 0.99 (d, 3H, J=5.9 Hz), 0.91 (d, 3H, J=6.9 Hz), 0.87 (d, 3H, J=6.8 Hz); $^{19}$F NMR (CD$_3$OD) δ −114.75 (dd, J=258, 9 Hz), −121.97 (dd, J=258, 17 Hz).

Scheme II step I; To a stirred solution of the above prepared macrocyclic alcohol (9 mg, 0.014 mmol) in 1:1 methylene chloride/acetonitrile (8 mL) under nitrogen is added the Dess-Martin periodinane (30 mg, 0.071 mmol). The resulting suspension is allowed to stir at room temperature for 3 days. The mixture is then diluted with ethyl acetate/aqueous sodium bicarbonate and sodium thiosulfate. After 10 minutes, the organic layer is separated, washed with water and concentrated under vacuum to provide a mixture of recovered alcohol, ketone and ketone hydrate. The mixture is resubjected to the oxidation reaction using periodinane (30 mg, 0.071 mmol) in 3:1 acetonitrile/methylene chloride (4 mL). After 7 days, the mixture is worked up as above to provide a mixture of the title compound and the hydrate of the title compound (6 mg total) as a white solid: $^{19}$F NMR (CD$_3$CN) δ ketone: −111.93 and −111.96 (2s, inner peaks of an AB pattern), ketone hydrate: −115.36 (d, J=257 Hz), −119.02 (d, J=257 Hz).

EXAMPLE 3

Preparation of N-Benzyl-3-(6-benzyl-9-isopropyl-4,7,10-trioxo-2-oxa-5,8,11-triaza-bicyclo[12.2.2]octadeca-1(17),14(18),15-trien-12-yl)-2,2-difluoro-3-oxo-propionamide

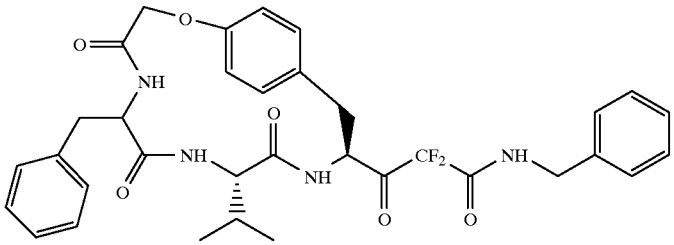

Scheme II steps C and D; A solution of [3ξ,4(S)]-2,4,5-trideoxy-4-[[(1,1-dimethylethoxy)carbonyl]amino]-2,2-difluoro-5-[4-[2-methoxy-2-(oxo)ethoxy]phenyl]-N-(phenylmethyl)-L-glycero-pentonamide (0.790 mmol, prepared in example 1 Scheme II step B) in trifluoroacetic acid (TFA) (4 mL) is allowed to stir under nitrogen for 2 hours. The solution is concentrated in vacuo and the residue is twice dissolved in EtOAc and concentrated again. The resulting TFA salt is dissolved in 1:1 $CH_2Cl_2$/DMF (3 mL) with stirring under nitrogen and 1-hydroxybenzotriazole hydrate (HOBT) (128 mg, 0.84 mmol), N-methylmorpholine (NMM) (190 µL, 1.73 mmol), Boc-phe-val-OH (0.84 mmol), and EDC (168 mg, 0.88 mmol) are added in that order. After 3 days, the mixture is poured into water and extracted twice with EtOAc. The combined extracts are washed with dilute aqueous HCl, $NaHCO_3$, and brine, and dried over anhydrous magnesium sulfate. The organic layer is concentrated under vacuum to provide the desired amide.

Scheme II steps E and F; To a stirred suspension of the above prepared amide (0.589 mmol) in 19:1 $CH_3OH/H_2O$ (20 mL) is added $LiOH.H_2O$ (34 mg, 0.81 mmol). After 2 hours, the solution is concentrated in vacuo. The residue is dissolved in water; the aqueous solution is washed with ether, is covered with EtOAc, and is acidified with vigorous stirring by the addition of 0.1 N $NaHSO_4$ (10 mL). The organic layer is separated, and the aqueous layer is extracted with a second portion of EtOAc. The combined organic layers are washed with brine and dried over anhydrous magnesium sulfate. The organic layer is concentrated under vacuum to provide the corresponding acid, which is dissolved in $CH_2Cl_2$ (5 mL). To this stirred solution under nitrogen is added $C_6F_5OH$ (139 mg, 0.755 mmol) and EDC (140 mg, 0.73 mmol). After 1 day the mixture is diluted with water and filtered, washing the solid with water and ether to provide the desired pentafluorophenyl ester. Alternatively the desired pentafluorophenyl ester can be isolated by extractive methods well known in the art.

Scheme II steps G and H: The above prepared pentafluorophenyl ester is suspended in 4 N HCl/dioxane (16 mL) with stirring. After 2 hours the solvent and HCl are removed in vacuo and the residual solid/gel is suspended in dilute aqueous $NaHCO_3/CH_2Cl_2$ with vigorous stirring for 3 days. The mixture is filtered, and the solids are washed with water and ether. Hot EtOAc is added along with just enough $CF_3CH_2OH$ to dissolve most of the solids; filtration through filter aid and concentration under vacuum provides the desired macrocyclic alcohol.

Scheme II step I: To a stirred solution of the above prepared macrocyclic alcohol (0.014 mmol) in 1:1 methylene chloride/acetonitrile (8 mL) under nitrogen is added the Dess-Martin periodinane (60 mg, 0.14 mmol). The resulting suspension is allowed to stir at room temperature for 3 days. The mixture is then diluted with ethyl acetate/aqueous sodium bicarbonate, sodium thiosulfate. After 10 minutes, the organic layer is separated, washed with water and concentrated under vacuum to provide the title compound.

EXAMPLE 4

Preparation of 3-[12-(Benzylcarbamoyl-difluoro-acetyl)-9-isopropyl-4,7,10-trioxo-2-oxa-5,8,11-triazabicyclo[12.2.2]octadeca-1(17),14(18),15-trien-6-yl]-propionic acid

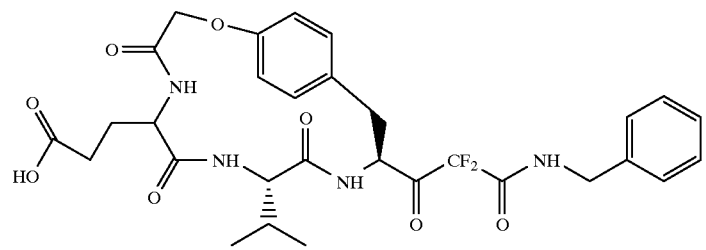

Scheme II step C; A solution of [3ξ,4(S)]-2,4,5-trideoxy-4-[[(1,1-dimethylethoxy)carbonyl]amino]-2,2-difluoro-5-[4-[2-methoxy-2-(oxo)ethoxy]phenyl]-N-(phenylmethyl)-L-glycero-pentonamide (0.790 mmol, prepared in example 1 Scheme II step B) in trifluoroacetic acid (TFA) (4 mL) is allowed to stir under nitrogen for 2 hours. The solution is concentrated in vacuo and the residue is twice dissolved in EtOAc and concentrated again to provide the TFA salt of the deprotected amine.

Scheme III step A; The TFA salt of the deprotected amine prepared above is dissolved in 1:1 CH$_2$Cl$_2$/DMF (3 mL) with stirring under nitrogen and 1-hydroxybenzotriazole hydrate (HOBT) (128 mg, 0.84 mmol), N-methylmorpholine (NMM) (190 μL, 1.73 mmol), Boc-val-OH (0.84 mmol), and EDC (168 mg, 0.88 mmol) are added in that order. After 3 days, the mixture is poured into water and extracted twice with EtOAc. The combined extracts are washed with dilute aqueous HCl, NaHCO$_3$, and brine, and dried over anhydrous magnesium sulfate. The organic layer is concentrated under vacuum to provide the desired amide.

Scheme III step B and C; A solution of the above prepared amide (0.790 mmol) in trifluoroacetic acid (TFA) (4 mL) is allowed to stir under nitrogen for 2 hours. The solution is concentrated in vacuo and the residue is twice dissolved in EtOAc and concentrated again to provide the TFA salt of the deprotected amine. The TFA salt of the deprotected amine is dissolved in 1:1 CH$_2$Cl$_2$/DMF (3 mL) with stirring under nitrogen and 1-hydroxybenzotriazole hydrate (HOBT) (128 mg, 0.84 mmol), N-methylmorpholine (NMM) (190 μL, 1.73 mmol), Nα-FMOC-γ-tert-butyl ester-glu-OH (0.84 mmol), and EDC (168 mg, 0.88 mmol) are added in that order. After 3 days, the mixture is poured into water and extracted twice with EtOAc. The combined extracts are washed with dilute aqueous HCl, NaHCO$_3$, and brine, and dried over anhydrous magnesium sulfate. The organic layer is concentrated under vacuum to provide the desired amide.

Alternative method for cyclization

The above prepared amide (0.6 mmol) is dissolved in methanol/water (19:1) and lithium hydroxide.H$_2$O (1.2 mmol) is added with stirring. After 5 hours the reaction is diluted with water and rinsed with ether. The aqueous layer is then acidified to pH 4.5-5 with 0.1N aqueous sodium bisulfate. The acidified aqueous layer is then extracted with ethyl acetate. The organic layer is dried over anhydrous magnesium sulfate, filtered and concentrated under vacuum to provide the desired acid/deprotected amine as shown below.

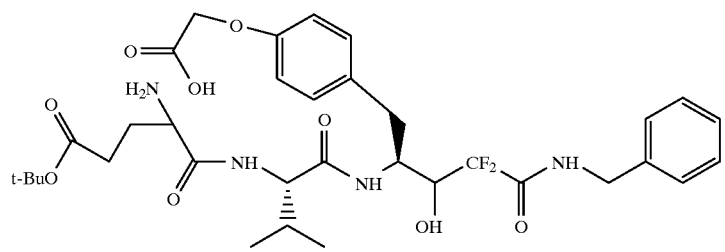

The above prepared acid/deprotected amine (0.70 mmol) is dissolved in 1:1 CH$_2$Cl$_2$/DMF (3 mL) with stirring under nitrogen and 1-hydroxybenzotriazole hydrate (HOBT) (128 mg, 0.84 mmol), N-methylmorpholine (NMM) (95 μL, 0.87 mmol) and EDC (168 mg, 0.88 mmol) are added in that order. After 3 days, the mixture is poured into water and extracted twice with EtOAc. The combined extracts are washed with dilute aqueous HCl, NaHCO$_3$, and brine, and dried over anhydrous magnesium sulfate. The organic layer is concentrated under vacuum to provide the macrocyclic alcohol.

Scheme II step I; To a stirred solution of the above prepared macrocyclic alcohol (0.014 mmol) in 1:1 methylene chloride/acetonitrile (8 mL) under nitrogen is added the Dess-Martin periodinane (60 mg, 0.14 mmol). The resulting suspension is allowed to stir at room temperature for 3 days. The mixture is then diluted with ethyl acetate/aqueous sodium bicarbonate, sodium thiosulfate. After 10 minutes, the organic layer is separated, washed with water and concentrated under vacuum to provide the ketone.

Scheme II step J; Dissolve the above prepared ketone (0.013 mmol) in methylene chloride (4 mL) and add trifluoroacetic acid (1 mL). Stir the reaction for 3 hours at room temperature and then concentrate under vacuum to provide the title compound.

EXAMPLE 5

Preparation of 3-[6-(4-Amino-butyl)-9-isopropyl-4,7,10-trioxo-2-oxa-5,8,11-triaza-bicyclo[12.2.2]octadeca-1(17),14(18),15-trien-12-yl]-N-benzyl-2,2-difluoro-3-oxo-propionamide

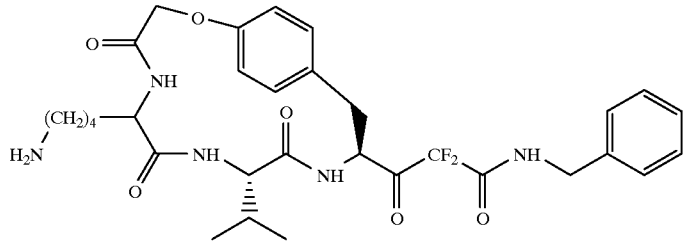

Scheme II steps C and D; A solution of [3ξ,4(S)]-2,4,5-trideoxy-4-[[(1,1-dimethylethoxy)carbonyl]amino]-2,2-difluoro-5-[4-[2-methoxy-2-(oxo)ethoxy]phenyl]-N-(phenylmethyl)-L-glycero-pentonamide (0.790 mmol, prepared in example 1 Scheme II step B) in trifluoroacetic acid (TFA) (4 mL) is allowed to stir under nitrogen for 2 hours. The solution is concentrated in vacuo and the residue is twice dissolved in EtOAc and concentrated again. The resulting TFA salt is dissolved in 1:1 $CH_2Cl_2$/DMF (3 mL) with stirring under nitrogen and 1-hydroxybenzotriazole hydrate (HOBT) (128 mg, 0.84 mmol), N-methylmorpholine (NMM) (190 µL, 1.73 mmol), Nα-t-Boc-NΔ-Cbz-L-lyx-val-OH (0.84 mmol), and DEC (168 mg, 0.88 mmol) are added in that order. After 1 day, the mixture is poured into water and extracted twice with EtOAc. The combined extracts are washed with dilute aqueous HCl, $NaHCO_3$, and brine, and dried over anhydrous magnesium sulfate. The organic layer is concentrated under vacuum to provide the desired amide.

Scheme II steps E and F; To a stirred suspension of the above prepare amide (0.589 mmol) in 19:1 $CH_3OH/H_2O$ (20 mL) is added $LiOH.H_2O$ (34 mg, 0.81 mmol). After 2 hours, the solution is concentrated in vacuo. The residue is dissolved in water; the aqueous solution is washed with ether, is covered with EtOAc, and is acidified with vigorous stirring by the addition of 0.1 N $NaHSO_4$ (10 mL). The organic layer is separated, and the aqueous layer is extracted with a second portion of EtOAc. The combined organic layers are washed with brine and dried over anhydrous magnesium sulfate. The organic layer is concentrated under vacuum to provide the corresponding acid, which is dissolved in $CH_2Cl_2$ (5 mL). To this stirred solution under nitrogen is added $C_6F_5OH$ (139 mg, 0.755 mmol) and EDC (140 mg, 0.73 mmol). After 1 day the mixture is diluted with water and filtered, washing the solid with water and ether to provide the desired pentafluorophenyl ester. Alternatively the desired pentafluorophenyl ester can be isolated by extractive methods well known in the art.

Scheme II steps G and H: The above prepared pentafluorophenyl ester is suspended in 4 N HCl/dioxane (16 mL) with stirring. After 2 hours the solvent and HCl are removed in vacuo and the residual solid/gel is suspended in dilute aqueous $NaHCO_3/CH_2Cl_2$ with vigorous stirring for 3 days. The mixture is filtered, and the solids are washed with water and ether. Hot EtOAc is added along with just enough $CF_3CH_2OH$ to dissolve most of the solids; filtration through filter aid and concentration under vacuum provides the desired macrocyclic alcohol.

Scheme II step I: To a stirred solution of the above prepared macrocyclic alcohol (0.014 mmol) in 1:1 methylene chloride/acetonitrile (8 mL) under nitrogen is added the Dess-Martin periodinane (60 mg, 0.14 mmol). The resulting suspension is allowed to stir at room temperature for 3 days. The mixture is then diluted with ethyl acetate/aqueous sodium bicarbonate, sodium thiosulfate. After 10 minutes, the organic layer is separated, washed with water and concentrated under vacuum to provide the desired ketone.

Scheme II step J; To a stirred suspension of Pd black (10 mg) in 4.4% $HCO_2H$/methanol (5 mL) is added the above prepared ketone (0.014 mmol). After 4 hours the reaction is filtered and the filtrate is concentrated under vacuum to provide the title compound.

EXAMPLE 6

Preparation of N-Benzyl-3-[6-(2-carbamoylethyl)-9-isopropyl-4,7,10-trioxo-2-oxa-5,8,11-triazabicyclo[12.2.2]octadeca-1(17),14(18),15-trien-12-yl]-2,2-difluoro-3-oxo-propionamide

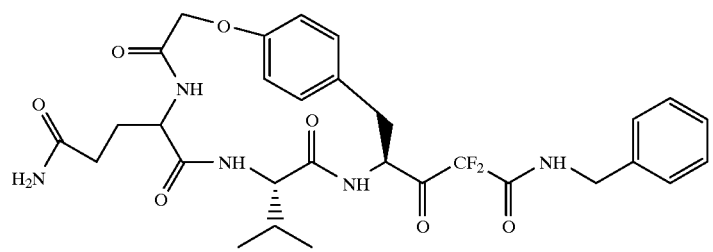

Scheme II steps C and D; A solution of [3ξ,4(S)]-2,4,5-trideoxy-4-[[(1,1-dimethylethoxy)carbonyl]amino]-2,2-difluoro-5-[4-[2-methoxy-2-(oxo)ethoxy]phenyl]-N-(phenylmethyl)-L-glycero-pentonamide (0.790 mmol, prepared in example 1 Scheme II step B) in trifluoroacetic acid (TFA) (4 mL) is allowed to stir under nitrogen for 2 hours. The solution is concentrated in vacuo and the residue is twice dissolved in EtOAc and concentrated again. The resulting TFA salt is dissolved in 1:1 $CH_2Cl_2$/DMF (3 mL) with stirring under nitrogen and 1-hydroxybenzotriazole hydrate (HOBT) (128 mg, 0.84 mmol), N-methylmorpholine (NMM) (190 µL, 1.73 mmol), Boc-gln-val-OH (0.84 mmol), and EDC (168 mg, 0.88 mmol) are added in that order. After 1 day, the mixture is poured into water and extracted twice with EtOAc. The combined extracts are washed with dilute aqueous HCl, $NaHCO_3$, and brine, and dried over anhydrous magnesium sulfate. The organic layer is concentrated under vacuum to provide the desired amide.

Scheme II steps E and F; To a stirred suspension of the above prepare amide (0.589 mmol) in 19:1 $CH_3OH/H_2O$ (20 mL) is added $LiOH.H_2O$ (34 mg, 0.81 mmol). After 2 hours, the solution is concentrated in vacuo. The residue is dissolved in water; the aqueous solution is washed with ether, is covered with EtOAc, and is acidified with vigorous stirring by the addition of 0.1 N $NaHSO_4$ (10 mL). The organic layer is separated, and the aqueous layer is extracted with a second portion of EtOAc. The combined organic layers are washed with brine and dried over anhydrous magnesium sulfate. The organic layer is concentrated under vacuum to provide the corresponding acid, which is dissolved in $CH_2Cl_2$ (5 mL). To this stirred solution under nitrogen is added $C_6F_5OH$ (139 mg, 0.755 mmol) and EDC (140 mg, 0.73 mmol). After 1 day the mixture is diluted with water and filtered, washing the solid with water and ether to provide the desired pentafluorophenyl ester. Alternatively the desired pentafluorophenyl ester can be isolated by extractive methods well known in the art.

Scheme II steps G and H: The above prepared pentafluorophenyl ester is suspended in 4 N HCl/dioxane (16 mL) with stirring. After 2 hours the solvent and HCl are removed in vacuo and the residual solid/gel is suspended in dilute aqueous $NaHCO_3/CH_2Cl_2$ with vigorous stirring for 3 days. The mixture is filtered, and the solids are washed with water and ether. Hot EtOAc is added along with just enough $CF_3CH_2OH$ to dissolve most of the solids; filtration through filter aid and concentration under vacuum provides the desired macrocyclic alcohol.

Scheme II step I: To a stirred solution of the above prepared macrocyclic alcohol (0.014 mmol) in 1:1 methylene chloride/acetonitrile (8 mL) under nitrogen is added the Dess-Martin periodinane (60 mg, 0.14 mmol). The resulting suspension is allowed to stir at room temperature for 3 days. The mixture is then diluted with ethyl acetate/aqueous sodium bicarbonate, sodium thiosulfate. After 10 minutes, the organic layer is separated, washed with water and concentrated under vacuum to provide the title compound.

In a further embodiment the present invention provides a method of treating a patient afflicted with a viral infection comprising the administration thereto of an effective antiviral amount of a compound of formula (I).

The term "viral infection" as used herein refers to an abnormal state or condition characterized by viral transformation of cells, viral replication and proliferation. Viral infections for which treatment with a compound of formula (I) will be particularly useful include retroviruses such as but not limited to HTLV-I, HTLV-II, HTLV-III (HIV virus), murine leukemia virus, feline leukemia virus, cytomegalovirus(CMV), avian sarcoma virus and the like. In addition treatment with a compound of formula (I) would be useful in treating a wide range of states of HIV infection: AIDS, ARC (AIDS related complex), both symptomatic and asymptomatic, and actual or potential exposure to HIV. For example, compounds of this invention are useful in treating symptomatic AIDS after suspected past exposure to HIV by, e.g., blood transfusion, accidental needle stick, or exposure to patient blood during surgery.

An "effective antiviral amount" of a compound of formula (I) refers to an amount which is effective, upon single or multiple dose administration to the patient, in controlling the growth of the virus or in prolonging the survivability of the patient beyond that expected in the absence of such treatment. As used herein "controlling a viral infection" refers to slowing, interrupting, arresting or stopping the viral transformation of cells or the replication and proliferation of the virus and does not necessarily indicate a total elimination of the virus.

The present invention further provides a method of inhibiting HIV protease in a patient in need thereof comprising administering to said patient an effective inhibitory amount of a compound of formula (I).

It is understood that patients suffering from a retrovirus, such as HTLV-III are in need of an HIV protease inhibitor such as a compound of formula (I).

As used herein, the term "patient" refers to a warm-blooded animal, such as a mammal, which is afflicted with a particular viral infection. It is understood that humans, mice and rats are included within the scope of the term "patient".

Administration of a compound of formula (I) to a patient results in inhibition of HIV protease in the patient. Thus, by treatment of a patient with a compound of formula (I) retroviruses, such as HTLV-III, are inhibited or suppressed.

A patient is in need of treatment with an agent which inhibits HIV protease, such as a compound of formula (I), where the patient is suffering from certain viral infections for which HIV protease is implicated as a contributing factor in the progression of the disease.

Based on standard clinical and laboratory tests and procedures, an attending diagnostician, as a person skilled in the art, can readily identify those patients who are in need of treatment with an agent which inhibits HIV protease, such as a compound of formula (I).

An "effective inhibitory amount" of a compound of formula (I) is that amount which is effective, upon single or multiple does administration to a patient, in providing an inhibition of HIV protease.

As used herein the term "effective amount" refers to an effective antiviral or inhibitory amount of a compound of formula (I). An effective amount can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific viral infection involved; the degree of or involvement or the severity of the viral infection; the response of the individual patient; the particular compound administered; the mode of administration; the bioavailability characteristics of the preparation administered; the dose regimen selected; the use of concomitant medication; and other relevant circumstances.

An effective amount of a compound of formula (I) is expected to vary from about 0.1 milligram per kilogram of body weight per day (mg/kg/day) to about 100 mg/kg/day. Preferred amounts are expected to vary from about 0.5 to about 10 mg/kg/day.

In effecting treatment of a patient afflicted with a viral infection, a compound of formula (I) can be administered in any form or mode which makes the compound bioavailable in effective amounts, including oral and parenteral routes. For example, compounds of formula (I) can be administered orally, subcutaneously, intramuscularly, intravenously, transdermally, intranasally, rectally, and the like. Oral administration is generally preferred. One skilled in the art of preparing formulations can readily select the proper form and mode of administration depending upon the particular characteristics of the compound selected, the viral infection to be treated, the stage of the infection, and other relevant circumstances.

The compounds of formula (I) can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable salts for purposes of stability, convenience of crystallization, increased solubility and the like.

In another embodiment, the present invention provides compositions comprising a compound of formula (I) in admixture or otherwise in association with one or more inert carriers. These compositions are useful, for example, as assay standards, as convenient means of making bulk shipments, or as pharmaceutical compositions. An assayable amount of a compound of formula (I) is an amount which is readily measurable by standard assay procedures and techniques as are well known and appreciated by those skilled in the art. Assayable amounts of a compound of formula (I) will generally vary from about 0.001% to about 75% of the composition by weight. Inert carriers can be any material which does not degrade or otherwise covalently react with a compound of formula (I). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising a therapeutically effective amount of a compound of formula (I) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The present invention is also directed to combinations of the HIV protease-inhibitory compounds with one or more agents useful in the treatment of AIDS, such as, for example, with known antiviral agents suitable for treating HIV 1 and HIV 2 viral infections, e.g., AZT, with or without a PNPase inhibitor, or in conjunctive therapy with DDI and a PNPase inhibitor.

The compounds of this invention may be assayed for their HIV-protease inhibition using the following techniques.

Preparation of Retroviral Enzyme and Assay for Inhibition of the Protease

A) Preparation of Retroviral Enzyme

To prepare the recombinant protease, the HIV protease is expressed via *E. Coli* by the published work of C. Guénet, et al., in *European Journal of Pharmacology, Molecular Pharmacology Section*, 172, 443–451,(1989). The recombinant enzyme was partially purified according to Darke, P. L. et al., *J. Biol. Chem.*, 256, 2307 (1989).

B) Enzyme Assay

The specific activity of the partially purified protease is in the range of 10–100 units per mg protein (one unit is defined as the amount of enzyme that will cleave one mole of H-Ser-Gln-Asn-Tyr-Pro-Ile-Val-$NH_2$ per minute at 37° C. under the assay conditions). HIV-1 is assayed against the octapeptide H-Ser-Gln-Asn-Tyr-Pro-Ile-Val-$NH_2$. The reaction is performed in 0.1 mL of a buffer containing 0.05 M sodium acetate, 0.5 M sodium chloride, 1 mM EDTA, 0.5% BSA, 5% ethyleneglycol, 10% glycerol, pH 5.5. The reaction is stopped after an incubation time of 1 hour at 37° C. via quenching with perchloric acid (final concentration 0.4M) and cetrifuged (Eppendorf) for 5 minutes. The products of the reaction, H-Ser-Gln-Asn-Tyr-OH ($P_1$) and H-Pro-Ile-Val-$NH_2$ ($P_2$), are analyzed by HPLC on a $C_{18}$ column (Ultrasphere ODS, 4.6×150 mm, 5 mm, Beckman), by integration of the corresponding peak areas. The elution is performed with an acetonitrile gradient (5% acetonitrile, pH 3.0 to 60% acetonitrile, pH 3.0 in 10 minutes, at a flow rate of 1 mL/min; retention times: $P_1$=6 minutes, $P_2$=7 minutes and S=8.3 minutes). $K_i$ values are determined from a Dixon plot (l/v versus [I]), see Segal, I. H., *Enzyme Kinetics*, 109 (1975). The $K_i$ for [(9S),12(S)]-α,α-Difluoro-9-(1-methylethyl)-β,4,7,10-tetraoxo-N-(phenylmethyl)-2-oxa-5,8,11,-triazabicyclo[12.2.2]octadeca-14,16,17-triene-12-propanamide=10 to 30 nM.

By following the techniques referenced above, as well as by utilization of other known techniques, as well as by comparison with compounds known to be useful for treatment of the above-mentioned disease states, it is believed that adequate material is available to enable one of ordinary skill in the art to practice the invention.

As with any group of structurally related compounds which possesses a particular generic utility, certain groups and configurations are preferred for compounds of formula (I) in their end-use application.

Compounds of formula (I) wherein X is 1 are generally preferred. Compounds of formula (I) wherein $P_3$ is —$CH_2CO_2H$, —$CH_2CONH_2$, —$CH_2(CH_2)_3NH_2$, —$CH_2CH_2CO_2H$, —$CH_2CH_2CONH_2$, benzyl and

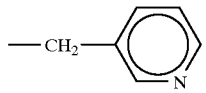

are generally preferred. Compounds of formula (I) wherein $P_2$ is —$CH(CH_3)_2$, cyclopentyl and phenyl are generally preferred. Compounds of formula (I) wherein the configuration about the carbon atom in the cyclic structure to which $P_3$ is attached is in the D configuration are generally preferred. Compounds of formula (I) in which $R_1$ is hydrogen and $R_2$ is benzyl, 2-pyridyl, 3-pyridyl and

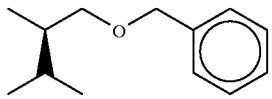

are generally preferred.

Examples of compounds according to the present invention are the following:

1) [(9S),12(S)]-α,α-Difluoro-9-(1-methylethyl)-β,4,7,10-tetraoxo-N-(phenylmethyl)-2-oxa-5,8,11,-triazabicyclo[12.2.2]octadeca-14,16,17-triene-12-propanamide;

2) [(9S),12(S)]-α,α-Difluoro-9-(1-methylethyl)-β,4,7,10-tetraoxo-N-[2-methyl-1-[(phenylmethoxy)methyl]propyl]-2-oxa-5,8,11,-triazabicyclo[12.2.2]octadeca-14,16,17-triene-12-propanamide;

3) N-Benzyl-3-(6-benzyl-9-isopropyl-4,7,10-trioxo-2-oxa-5,8,11-triaza-bicyclo[12.2.2]octadeca-1(17),14(18),15-trien-12-yl)-2,2-difluoro-3-oxo-propionamide;

4) 3-[12-(Benzylcarbamoyl-difluoro-acetyl)-9-isopropyl-4,7,10-trioxo-2-oxa-5,8,11-triazabicyclo[12.2.2]octadeca-1(17),14(18),15-trien-6-yl]-propionic acid;

5) 3-[6-(4-Amino-butyl)-9-isopropyl-4,7,10-trioxo-2-oxa-5,8,11-triaza-bicyclo[12.2.2]octadeca-1(17),14(18),15-trien-12-yl]-N-benzyl-2,2-difluoro-3-oxo-propionamide;

6) N-Benzyl-3-[6-(2-carbamoylethyl)-9-isopropyl-4,7,10-trioxo-2-oxa-5,8,11-triazabicyclo[12.2.2]octadeca-1(17),14(18),15-trien-12-yl]-2,2-difluoro-3-oxo-propionamide;

7) [12-(Benzylcarbamoyl-difluoro-acetyl)-9-isopropyl-4,7,10-trioxo-2-oxa-5,8,11-triazabicyclo[12.2.2]octadeca-1(17),14(18),15-trien-6-yl]-acetic acid;

8) N-Benzyl-3-(6-carbamoylmethyl-9-isopropyl-4,7,10-trioxo-2-oxa-5,8,11-triazabicyclo[12.2.2]octadeca-1(17),14(18),15-trien-12-yl)-2,2-difluoro-3-oxo-propionamide;

9) N-Benzyl-2,2-difluoro-3-(9-isopropyl-4,7,10-trioxo-6-pyridin-3-ylmethyl-2-oxa-5,8,11-triazabicyclo[12.2.2]octadeca-1(17),14(18),15-trien-12-yl)-3-oxo-propionamide;

and the stereoisomers, hydrates and pharmaceutically acceptable salts thereof.

What is claimed is:

1. A compound of the formula:

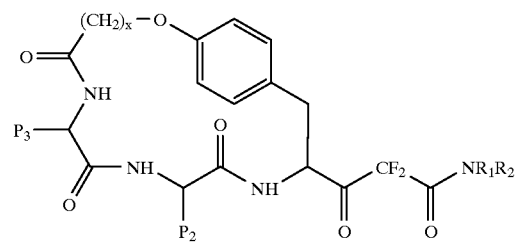

and the stereoisomers, hydrates, and pharmaceutically acceptable salts thereof wherein $P_2$ is $C_{1-6}$ alkyl, cyclopentyl, hydroxy $C_{1-6}$ alkyl, phenyl, benzyl or 3-tetrahydrofuryl;

$P_3$ is selected from the group consisting of hydrogen, —$CH_3$, —$CH(CH_3)_2$, —$CH_2CH(CH_3)_2$, —$CH(CH_3)(CH_2CH_3)$, —$CH_2SH$, —$CH_2CH_2SCH_3$, —$CH_2OH$, —$CH(CH_3)OH$, —$CH_2(CH_2)_3NH_2$, —$CH_2(CH_2)_2NHC(=NH)NH_2$, —$CH_2CO_2H$, —$CH_2CH_2CO_2H$, —$CH_2CONH_2$, —$CH_2CH_2CONH_2$, benzyl,

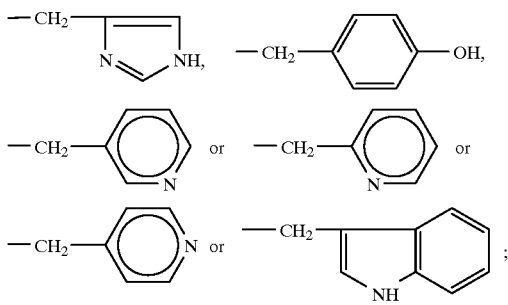

$R_1$ is hydrogen, $C_{1-15}$ alkyl, hydroxy $C_{1-15}$ alkyl, $CH([(CH_2)_d-O-CH_2]_f-R_7)_2$, $CH_2Si(CH_3)_2(R_8)$, PDL, $-(C_{1-6}$ alkylene$)-OR_4$, $CH(Y)(Z)$,

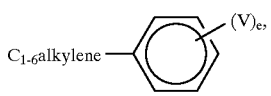 (a)

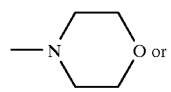 or (c)

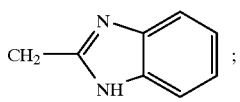 ; (d)

wherein PDL is $-(CH_2)_a$-2-, 3- or 4-pyridyl; Y is hydroxy $C_{1-15}$ alkyl, $C_{1-6}$ alkyl or $(CH_2)_e$-$C_6H_4$-$(V)_{e'}$; Z is $(CH_2)_d$-O-CHO, $C_{1-6}$ alkylene-O-$(CH_2)_d$-(O-$CH_2$-$CH_2)_e$-O-$C_{1-6}$ alkyl, CHO, $CO_2R_4$, $CONHR_4$, $(CH_2)_d$-O-$(CH_2)_d$-$R_5$, $(CH_2)_e$-$OR_4$ or

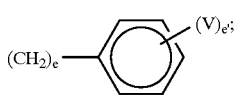 ; (e)

wherein V is $OR_4$ or hydroxy $C_{1-6}$ alkylene; provided that d'=2 when $R_5$ is piperazinyl, substituted piperazinyl, piperidyl or morpholinyl;

$R_2$ is as defined for $R_1$ with the proviso that $R_2$ is other than hydrogen when $R_1$ is hydrogen, or $R_1$ and $R_2$ taken together with the nitrogen atom to which they are attached are selected from the group consisting of;

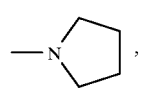 , (f)

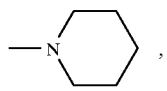 , (g)

 or (h)

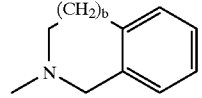 (i)

$R_4$ is hydrogen, $C_{1-6}$ alkyl, phenyl or benzyl;
$R_5$ is piperazinyl, substituted piperazinyl, piperidyl, morpholinyl, pyridyl, pyrazinyl, pyrimidinyl or phenyl, wherein substituted piperazinyl is piperazinyl substituted on one nitrogen atom thereof with CHO, C(O) $NHR_4$, $C_{1-4}$ alkyl or $CO_2R_4$;
$R_7$ is pyrimidyl, pyridyl, pyrazinyl or phenyl;
$R_8$ is $C_{1-6}$ alkylene, hydroxy $C_{1-6}$ alkyl or $C_{1-6}$ alkyl;
a is zero, 1, 2 or 3;
b is zero or 1;
d and d' are each independently 1 or 2;
e and e' are each independently zero, 1 or 2;
f is zero or one; and
x is 1, 2, 3, or 4.

2. A compound according to claim 1 wherein X is 1.
3. A compound according to claim 2 wherein $P_2$ is $-CH(CH_3)_2$.
4. A compound according to claim 3 wherein $R_1$ is hydrogen and $R_2$ is benzyl.
5. A compound according to claim 3 wherein $R_1$ is hydrogen and $R_2$ is 2-(3-methyl-1-phenylmethoxy)butyl.
6. A compound according to claim 4 wherein $P_3$ is hydrogen.
7. A compound according to claim 4 wherein $P_3$ is $CH_2CO_2H$.
8. A compound according to claim 4 wherein $P_3$ is $CH_2CONH_2$.
9. A compound according to claim 4 wherein $P_3$ is $CH_2CH_2CO_2H$.
10. A compound according to claim 4 wherein $P_3$ is $CH_2CH_2CONH_2$.
11. A compound according to claim 4 wherein $P_3$ is benzyl.
12. A compound according to claim 4 wherein $P_3$ is

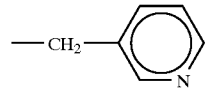

13. A compound according to claim 4 wherein $P_3$ is $-CH_2(CH_2)_3NH_2$.
14. A compound according to claim 4 wherein the carbon atom in the macrocyclic ring to which $P_3$ is attached, is in the D configuration.
15. A compound according to claim 1 wherein the compound is [9(S),12(S)]-α,α-Difluoro-9-(1-methylethyl)-β,4,7,10-tetraoxo-N-(phenylmethyl)-2-oxa-5,8,11,-triazabicyclo[12.2.2]octadeca-14,16,17-triene-12-propanamide.
16. A compound according to claim 1 wherein the compound is [9(S),12(S)]-α,α-Difluoro-9-(1-methylethyl)-β,4,7,10-tetraoxo-N-[2-methyl-1-[(phenylmethoxy)-methyl]propyl]-2-oxa-5,8,11,-triazabicyclo[12.2.2]octadeca-14,16,17-triene-12-propanamide.

* * * * *